(12) United States Patent
Beetge

(10) Patent No.: US 7,373,276 B2
(45) Date of Patent: May 13, 2008

(54) QUANTITATIVE EVALUATION OF EMULSION STABILITY BASED ON CRITICAL ELECTRIC FIELD MEASUREMENTS

(75) Inventor: Jannie Beetge, Pearland, TX (US)

(73) Assignee: Champion Technologies, Inc., Houston, TX (US)

( * ) Notice: Subject to any disclaimer, the term of this patent is extended or adjusted under 35 U.S.C. 154(b) by 39 days.

(21) Appl. No.: 11/302,800

(22) Filed: Dec. 13, 2005

(65) Prior Publication Data

US 2006/0129341 A1  Jun. 15, 2006

Related U.S. Application Data

(60) Provisional application No. 60/635,677, filed on Dec. 13, 2004.

(51) Int. Cl.
*G01C 17/12* (2006.01)
(52) U.S. Cl. .................... 702/182; 204/556
(58) Field of Classification Search .......... 702/2, 702/6, 11, 12, 22, 23, 57, 72, 99, 182, 183; 204/554–556, 164, 458
See application file for complete search history.

(56) References Cited

U.S. PATENT DOCUMENTS

| | | | | |
|---|---|---|---|---|
| 4,624,763 A * | 11/1986 | Chimenti | ............. | 204/562 |
| 4,981,569 A * | 1/1991 | Schugerl et al. | ............. | 204/673 |
| 5,283,001 A * | 2/1994 | Gregoli et al. | ............. | 516/67 |
| 5,435,920 A * | 7/1995 | Penth | ............. | 210/708 |
| 5,580,464 A * | 12/1996 | Bailes | ............. | 204/564 |
| 5,582,700 A * | 12/1996 | Bryning et al. | ............. | 204/450 |
| 5,607,574 A * | 3/1997 | Hart | ............. | 208/188 |
| 5,868,939 A * | 2/1999 | Oder et al. | ............. | 210/695 |
| 6,068,054 A * | 5/2000 | Bragg | ............. | 166/270 |
| 6,860,979 B2 * | 3/2005 | Sams | ............. | 204/556 |
| 2002/0101244 A1 | 8/2002 | Dahms | | |
| 2003/0206024 A1 | 11/2003 | Murphy, Jr. et al. | | |

OTHER PUBLICATIONS

Journal of Membrane Science vol. 128, May 1997; pp. 1-6; XP004068489; "Break-down of liquid membrane emulsion under high electric field"; Lu Gang, Lu QiongHua, Li PanSheng.

(Continued)

*Primary Examiner*—Edward Raymond
*Assistant Examiner*—Mohamed Charioui
(74) *Attorney, Agent, or Firm*—Jeffrey L. Streets; Streets & Steele

(57) ABSTRACT

A method for quantitative evaluation of emulsion stability using Critical Electric Field (CEF) determinations over a range of conditions, such as a range of temperatures, demulsifier compositions, or demulsifier concentrations. The method includes determining the CEF for a series of emulsions that differ substantially only in their internal phase volume ratio. A plot of CEF values as a function of the inverse of the internal phase volume ratio is characterized by a linear slope. Using the slope, a theoretical CEF value can be determined by extrapolating to where the inverse of the internal phase volume ratio is about one. The slope for a given emulsion series is associated with the relative energy barrier to flocculation and the theoretical critical electric field for a given emulsion series is associated with the relative energy barrier to coalescence. Comparative studies are performed using this method.

35 Claims, 23 Drawing Sheets

Introduction: Principle of IPR - CEF

OTHER PUBLICATIONS

Proceedings of 2002 IEEE 14th International Conference on Dielectric Liquids (ICDL 2002), Graz (Austria), Jul. 7-12, 2002; "Instability of electrically stressed water droplets in oil"; Gunnar Berg, Lars E. Lundgaard, et al.

Colloid and Surfaces A; pp. 33-47; "Crude oil emulsions in high electric fields as studied by dielectric spectroscopy. Influence of interaction between commercial and indigenous surfactants"; Harald Fordedal, et al.

Journal of Colloid and Interface Science vol. 225, pp. 494-504; May 2000; "Quantitative Determination of Asphaltenes and Resins in Solution by Means of Near-Infrared Spectroscopy. Correlations to Emulsion Stability"; Harald Kallevik, et al.

The PCT International Search Report; Apr. 2005.

PCT/US2005/045261, International Preliminary Report on Patentability Jun. 21, 2007.

Kallevik H, Olav M Kvalheim and Johan Sjöblom, Quantitative determination of asphaltenes and resins in solution by means of near-infrared spectroscopy. Correlations to emulsion stability; Journal of Colloid and Interface Science 494-504 (2000), May 25, 1999, Staoil R&D Centre, Rotvoll, N-7005 Trondheim, Norway and Department of Chemistry, University of Bergen Allegaten 41 41, N-5007 Bergen, Norway.

Fordedal Harald, Yannick Schildberg, Johan Sjöblom and Jean-Luc Volle: Crude oil emulsions in high electric fields as studied by dielectric spectroscopy. Influence of interaction between commercial and indigenous surfactants, Colloids and Surfaces A: Physicochemical and Engineering Aspects 106 (1196 33-47Mar. 10, 1995.

PCT International Preliminary Report on Patentability Jun. 21, 2007.

* cited by examiner

Introduction: Principle of IPR - CEF

QUANTITATIVE EVALUATION OF EMULSION STABILITY BASED ON CRITICAL ELECTRIC FIELD MEASUREMENTS

The present application claims priority of U.S. provisional patent application Ser. No. 60/635,677 filed on Dec. 13, 2004.

BACKGROUND OF THE INVENTION

1. Field of the Invention

The present invention relates to emulsion stability evaluation and the development of chemical demulsifiers.

2. Background of the Related Art

The inevitable creation and subsequent resolution of water-in-oil emulsions during the production and processing of crude oils are of significant importance in the oil field industry. These emulsions, which could typically be any combination of water-in-oil, oil-in-water, or complex emulsions, are very diverse in their nature and stability. The majority of oil field emulsions are resolved by the application of chemical demulsifiers in special processes under specific conditions. The stability of crude oil emulsions is influenced by a large number of variables and chemical demulsifiers are therefore specifically developed for each application, to achieve optimum economic efficiency.

Emulsion stability of water-in-oil emulsions encountered in the oil field industry can be evaluated using various methods, for example, the determination of droplet size and distribution by various methods, determining the amount of water resolved as a second phase, moisture analysis of the oil phase as well as more sophisticated methods such as interfacial rheology.

The use of Critical Electric Field (CEF) has recently been used to compare the stability of water-in-oil emulsions. With the CEF technique, a sample of water-in-oil emulsion is injected between two parallel electrode plates. A direct current voltage is applied between the two electrodes and increased in incremental steps, with continuous monitoring of the conductivity or electrical current through the oil sample. In response to the increasing applied electric field, the water droplets tend to align themselves to form agglomerated columns of droplets, which form a conducting bridge once a critical voltage (or electric field) has been reached. The strength of the electric field at which the sample shows a sharp increase in conductivity (increase in current through sample, between the two electrode plates) is recorded as the "Critical Electric Field". By this method, relative emulsion stability is quantitatively compared in terms of the CEF-value and expressed in units of $kV\ cm^{-1}$.

Demulsification processes may be described in terms of a few basic steps. Most often, these steps will include flocculation, coalescence and sedimentation. In some cases, aggregation or coagulation are preferred above flocculation to indicate specific qualities or properties of a pair or group of droplets. However, the term "flocculation," as used herein, is considered to be the reversible formation of a droplet pair or cluster, with virtually no change in the total oil/water interface area and is intended to encompass, without limitation, aggregation, coagulation, and agglomeration. Coalescence is defined here as the complete association of two droplets to form a single droplet by rupturing the thin film that separated the two droplets. Sedimentation implies settling of the coalesced droplets or flocculated group of droplets under gravitational influence. Large droplet sizes, high differences in density and low viscosity of the external phase favours sedimentation of droplets, which can proceed along three main routes. First, individual droplets can settle without any flocculation or coalescence. Second, individual droplets can flocculate or coagulate to settle as flocculated pairs or clusters of droplets. Third, flocculated pairs or groups of droplets can coalesce to settle as a single larger drop or group of enlarged drops.

Stokes law dictates that the settling rate of a spherical droplet will be proportional to the density difference between the drop and the continuous phase as well as proportional to the square of the drop radius. This implies that the settling of a droplet aggregate will be faster than an individual droplet, but slower than its equivalent, single coalesced droplet.

In reality, any demulsification process will be a complex combination of steps and will be determined by a large number of variables. However, for practical purposes, emulsion stability is considered to depend on the degree of flocculation and coalescence. Since sedimentation can also proceed from the flocculated pair, both flocculation and coalescence can act as parallel pathways to sedimentation. In the case of a gravitational settling process, the rate of demulsification (or mechanism) is not practically controlled or limited by the coalescence process as the only route to emulsion resolution. The stability of water-in-oil emulsions, as observed under conditions of gravitational settling, therefore generally depends on the ability or tendency of the water drops to form bigger droplets by flocculation and subsequent coalescence The majority of oil field emulsions are thermodynamically unstable. Thus, emulsion stability could in essence be described as a kinetic phenomenon, where emulsion stability is an expression used to describe the rate of phase separation for a given emulsion. Water-in-oil emulsions with high water settling rates are referred to as unstable emulsions, whereas emulsions with settling rates well outside the time domain of the observation, would be called stable emulsions.

SUMMARY OF THE INVENTION

One embodiment of the invention provides a method comprising: determining a critical electric field value for each emulsion in an emulsion series including emulsions that differ substantially only by internal phase volume ratios; and evaluating a line fit to the critical electric field values as a function of the inverse of the internal phase volume ratio for each emulsion in the emulsion series, wherein the step of evaluating further comprises determining the slope of the line, extrapolating the line to determine a theoretical critical electric field value at an internal phase volume ratio of about one, or combinations thereof. The method may further comprise identifying the slope of the line as a relative indicator of the flocculation energy barrier for the emulsion series and/or identifying the theoretical critical electric field value as a relative indicator of the coalescence energy barrier for the emulsion series.

Another embodiment provides a method comprising: determining a critical electric field value for each emulsion in a plurality of emulsion series, each emulsion series including emulsions that differ substantially only by internal phase volume ratios, and each emulsion series differing from each other emulsion series by a parameter of the emulsion other than internal phase volume ratio; and evaluating, for each emulsion series, a line fit to the critical electric field values as a function of the inverse of the internal phase volume ratio for each emulsion in the emulsion series, wherein the step of evaluating further comprises determining the slope of the line, extrapolating the line to determine a theoretical critical electric field value at an internal phase volume ratio of about one, or combinations thereof.

DETAILED DESCRIPTION OF A PREFERRED EMBODIMENT

In analogy to kinetic theory of chemical reactions, but on a macroscopic level, the mechanism of demulsification can be described as a process where the collision of two water droplets gives rise to an activated state. The activated state can then either "decompose" into the original two droplets or proceed irreversible to form a flocculated drop pair, establishing a concentration equilibrium condition for the activated state.

The formation of an activated state would require a certain amount of energy, analogous to activation energy. In a subsequent consecutive and irreversible step, the flocculated drop pair can coalesce to form a larger single drop. Formation of the activated step associated with coalescence would require an additional amount of energy. If the amount of energy required for the formation of the activated state of coalescence, is much less than that for flocculation, it could be expected that the coalescence step would be fast and that the rate-limiting step for demulsification will be flocculation. In this case the mechanism of demulsification could be considered as flocculation-controlled.

Figure 1:
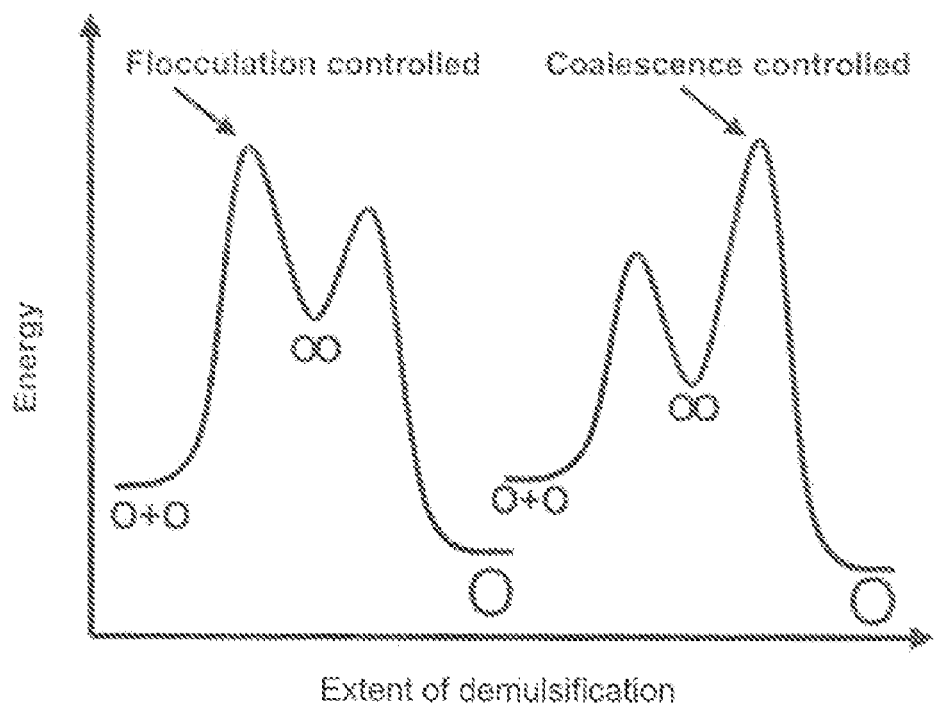
FIG. 1 is conceptual graph of the amount of energy required to break the emulsion by a process such as CEF.

By contrast, if the energy required for the formation of the activated state in the coalescence step is much higher than the amount of energy required for the activated state of flocculation, it could be expected that coalescence would be slower than flocculation and the demulsification process will be coalescence-controlled. FIG. 1 graphically presents the concept that the amount of energy required to break the emulsion by a process, such as CEF, is additive in the case of a coalescence-controlled mechanism of demulsification. A system of two droplets approaching each other will pass through an energy barrier, the activated state, to form a metastable droplet pair. The droplet pair can then proceed through a subsequent energy barrier, or activated state, to form a single larger droplet. The first energy barrier is associated with flocculation and the second energy barrier is associated with the coalescence process. Two hypothetical cases are presented in FIG. 1, for typical flocculation and coalescence controlled demulsification processes.

Naturally, the actual mechanism of demulsification is much more complex than suggested by FIG. 1. Since larger coalesced droplets, as well as groups of flocculated droplets, can also be involved in the collisions, it is possible that a very wide variety of activated states could exist at any point in time. These activated states will be very different in their stability and the nature of their products. However, it is believed that throughout this variety of interactions, there would be a preferred pathway associated with the lowest activation energy, for each step in the demulsification process.

The present invention provides an improved method to evaluate emulsions, such as crude oil emulsions, that lends itself to evaluation and development of chemical demulsifiers.

Critical Electric Field (CEF) Measurements

CEF data was calculated from measurements made with an OFITE Model ESM-30B Electrical Stability Tester. The instrument is configured as a submersible probe, connected to a battery powered control unit. The probe contains two parallel plate electrodes, spaced at a distance of 0.159 cm, on the inside of a cavity at the tip of the probe. CEF measurements were made with the probe fully submersed in an emulsion. A sinusoidal voltage was applied to the electrodes and ramped up at a constant rate of 150 Volts per second, to the instrument's voltage limit of 2 kV. A constant frequency of 340 Hz is maintained for the ramping potential difference. For the configuration of this instrument, a voltage of 2 kV corresponds with a maximum electric field strength of ~12.6 kV cm$^{-1}$. The conductivity or current through the sample was continuously monitored to detect the threshold value of 61 microampere, which was pre-selected as the dielectric breakdown voltage. At this level of conductivity, the sample was considered to become conductive, indicating droplet coalescence in the CEF application. The final CEF value was calculated from the "critical voltage" observed at a known constant distance between the two plates and expressed as the Critical Electric Field, in units of kV cm$^{-1}$.

All experimental work was performed on crude oil samples collected at active production facilities from offshore China. Crude oil emulsions were made up from five different crude-oil blends (labeled blend 1 to blend 5). These blends ranged in specific gravity between 0.856 to 0.916, with API gravity between 33.8 and 23.0. The wax content ranged between 23.35% and 31.43%, with cloud point ranging from 77° F. to 90° F. Ashphaltene content ranged from 0.33% to 0.90%, with a solids content range of 0.08% to 0.16%. Water content ranged from 0 to 0.4%. Each emulsion contained various synthetic brine concentrations from 10% to 70% at increments of 10%. The synthetic brine was made up to match the composition of the produced water. Emulsions were made up at three temperatures of 120° F., 150° F. and 180° F., using a Camframo BDC6015 stirrer unit equipped with a 50 mm Rushton type paddle. The procedure involved an agitation rate of 3000 RPM, maintained for a period of 5 minutes. A number of CEF measurements were made on each emulsion at room temperature to determine the average value as well as the standard deviation for each CEF determination.

A range of potential chemical demulsifiers were selected for testing. Stable crude oil emulsions were made up with a Chandler Model 30-60 constant speed mixer to contain various concentrations of synthetic brine. All emulsions were made up under identical conditions at a constant speed of 12,000 RPM, which was maintained for 60 seconds. CEF measurements were made at constant intervals of 1 minute. Fresh emulsions were treated with the different chemical demulsifiers at dose levels between 25 and 400 ppm followed by subsequent CEF determinations.

Figure 2:
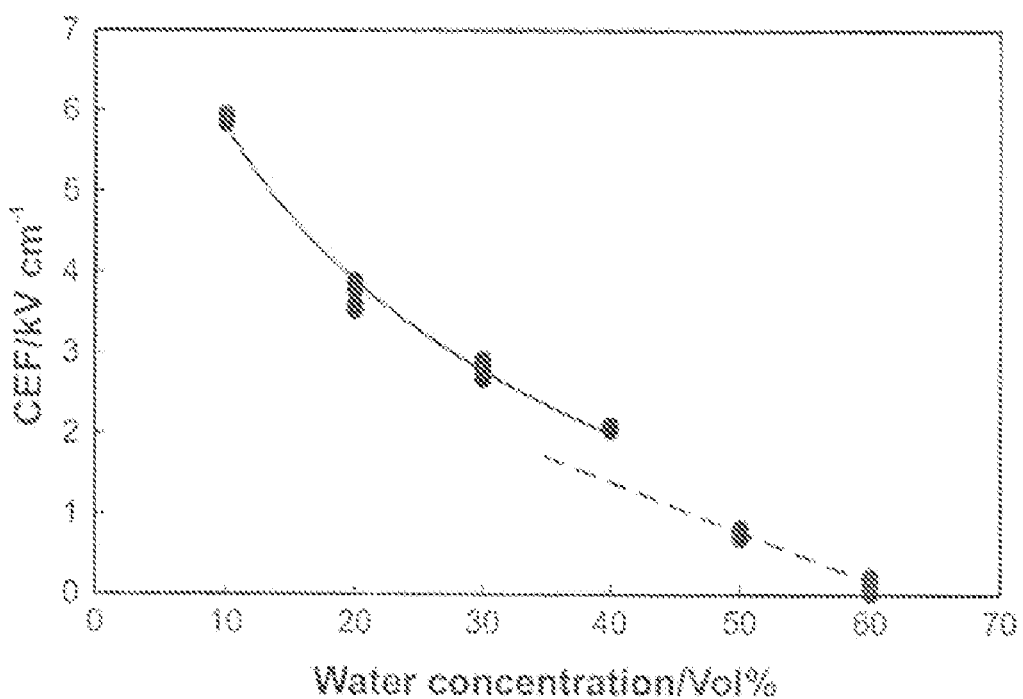
FIG. 2 is a graph of CEF measurements made on emulsions with different water content.

It was found that CEF measurements are normally high for emulsions with low water content, but that the observed CEF values decrease at higher water content. An example of typical results from the experimental work is shown in FIG. 2. The results in FIG. 2 were observed for emulsions with water content range between 10 and 60 vol %, made up from blend 4 at 120° F. A disconnect in the typical curve is sometimes noticeable at higher water content and explained in terms of partial reverse emulsion formation. The appearance of a reverse emulsion component at the point of deviation, above a water content of 40 vol %, was confirmed by a positive result for a typical oil-in-water emulsion test. The lines in FIG. 2 are added as a visual aid. Six CEF-measurements were made for each emulsion and indicated as graphical representations of the typical precision achieved with the CEF technique applied in this study.

Internal Phase Ratio-Critical Electric Field (IPR-CEF) Technique

In accordance with the invention, the stability of an emulsion in a flocculation-controlled emulsion-breaking process is considered to be inversely proportional to the probability of a collision between droplets if all other variables are kept constant. Low probability of a collision between droplets is associated with high emulsion stability and vice versa.

$$\text{Emulsion stability} \propto 1/\text{probability of a collision} \qquad \text{Equation (1)}$$

But, the probability of a collision, P, can also be expressed as the ratio of the number of droplets present, n, to the number of possible arrangements, g (the number of positions one droplet can occupy).

$$P = n/g \qquad \text{Equation (2)}$$

The number of possible arrangements for a specific droplet can be calculated as the total volume of the system, divided by the volume of a single drop, $V_d$. The total volume of the system is the sum of the volume of the internal phase, $V_i$, and the volume of the external phase, $V_e$.

$$g = (V_i + V_e)/V_d \qquad \text{Equation (3)}$$

However, the volume of a single droplet can be approximated as the volume of the internal (or dispersed) phase, $V_i$, divided by the number of droplets, n.

$$V_d = V_i/n \qquad \text{Equation (4)}$$

By substitution of equations 2, 3 and 4 into equation 1, it can be shown that, $$\text{Emulsion stability} \propto (V_i + V_e)/V_i \qquad \text{Equation (5)}$$

But $(V_i + V_e)/V_i$ is the inverse of the internal phase ratio, ϕ, where, $$\phi = V_i/(V_i + V_e) \qquad \text{Equation (6)}$$

The internal phase ratio is independent of the size or size distribution of the droplets and can be related to the probability of a collision between two droplets. Therefore, emulsion stability has been determined to be proportional to the inverse of the internal phase ratio (i.e., the free volume ratio).

$$\phi \text{ Emulsion stability} \propto 1/\phi \qquad \text{Equation (7)}$$

Thus, if the experimentally determined CEF-value is linear in its response and directly proportional to emulsion stability, it follows that the CEF-value is proportional to the inverse of the internal phase volume ratio.

$$\text{CEF-value} \propto 1/\phi \qquad \text{Equation (8)}$$

Furthermore, for a purely flocculation-controlled mechanism of demulsification, the emulsion stability will approach zero as the probability of collision approaches certainty (100% chance of a collision). But, probability of collision approaches certainty, when internal phase volume ratio approaches unity. Thus, the experimental CEF-value is expected to be zero at $V_{1/\phi} = 1$. Hypothetically, as the total volume of water droplets are increased to a level close to the total volume available in the system, the probability of collision is almost certain (very high internal phase volume ratio, i.e., ϕ approximately 1, which can be visualized as a very close packing of flocculated droplets). Of course, this condition cannot be practically achieved by experimentation, but the emulsion stability at such conditions is estimated by backward extrapolation of experimental CEF data to $1/\phi=1$.

Therefore, a linear relationship is expected for a plot of CEF value against the inverse of the internal phase volume ratio. It is believed that the slope of this plot will be a quantitative indication of the energy associated with the flocculation step and that the extrapolated CEF-value at $V_{1/\phi}=1$, will be a quantitative indication of the energy associated with the coalescence step in the mechanism of demulsification. As discussed later, it is preferred to obtain an extrapolated CEF value at $V_{1/\phi}=$about 1.35. However, whether the value of 1, 1.35 or some other value is used, the extrapolated CEF value may still be useful. Still, the CEF value at $V_{1/\phi}=1.35$ is preferred as being the most accurate indication of the energy associated with the coalescence step of demulsification. A deviation from the linear relationship at lower IPR-1 could be an indication of the degree of inverse emulsion formation.

EXAMPLE 1

CEF data collected for emulsions made up from blend 1, with the corresponding conditions of temperature and water content as well as the calculated value of $1/\phi$, are given in Table 1. The data in Table 1 is also graphically presented in FIG. 3, as a plot of CEF against $1/\phi$. The water content in Table 1 is limited to 40% as emulsions made up with blend 1 were very unstable at water concentrations above 40%, where quick phase separation and a substantial volume of a free water phase were observed. Experimental errors are not indicated in FIG. 3, but can be found in Table 1.

TABLE 1

CEF data on water-in-oil emulsions, made up from blend 1.

| Temperature/ °F. | Water content/% | CEF/ kV cm-1 | $1/\phi$ |
|---|---|---|---|
| 120 | 10 | (12.3 ± 0.5) | 10.0 |
|  | 20 | (5.2 ± 0.3) | 5.0 |
|  | 30 | (4.1 ± 0.2) | 3.33 |
|  | 40 | (2.70 ± 0.05) | 2.5 |
| 150 | 10 | (10.2 ± 0.2) | 10.0 |
|  | 20 | (5.6 ± 0.2) | 5.0 |
|  | 30 | (2.71 ± 0.04) | 3.33 |
|  | 40 | (2.04 ± 0.06) | 2.5 |
| 180 | 10 | (3.70 ± 0.02) | 10.0 |
|  | 20 | (2.20 ± 0.08) | 5.0 |
|  | 30 | (0.92 ± 0.04) | 3.33 |
|  | 40 | (0.61 ± 0.01) | 2.5 |

Figure 3:
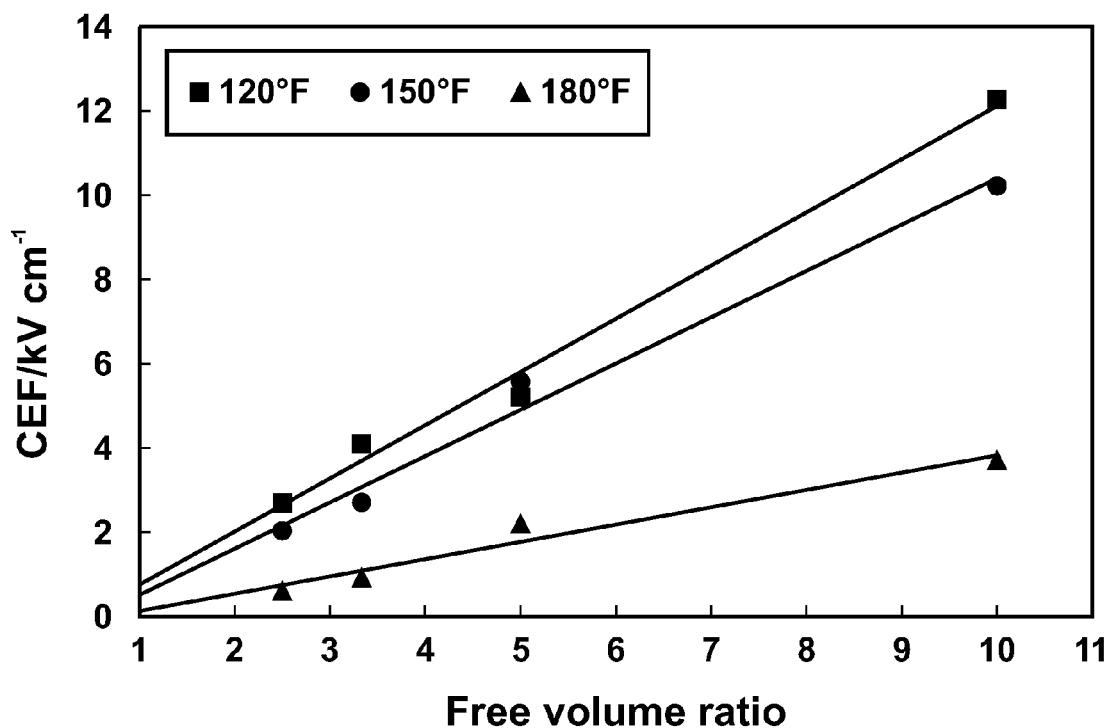
FIG. 3 is a plot of CEF against $1/\phi$.

The observed liner relationship between CEF and $1/\phi$ in FIG. 3 illustrates a flocculation-controlled emulsion breaking mechanism, as described above. This observation also confirms that the CEF technique does indeed provide a linear response in this application and that the relative numbers generated by this method could be used for quantitative comparison of emulsion stability. The slope of the plot in FIG. 3 gives an indication of the relative probability that a collision between two droplets will lead to flocculation. The observed CEF-values at a $V_{1/\phi}=1$ are positive, but small. This is explained as the result of a primarily flocculation-controlled emulsion breaking mechanism, where coalescence requires a relative small amount of energy.

CEF data collected on emulsions made up from blend 5, as well as the corresponding conditions of temperature and water content are given in Table 2. Some of the data collected is also graphically presented in FIG. 4, as a plot of CEF against $1/\phi$.

TABLE 2

CEF data for some water-in-oil emulsions, made up from blend 5, at different temperatures.

| Temperature/ °F. | Water content/% | CEF/ kV cm-1 | $1/\phi$ |
|---|---|---|---|
| 120 | 10 | (7.72 ± 0.09) | 10.0 |
|  | 20 | (4.57 ± 0.05) | 5.0 |
|  | 30 | (3.14 ± 0.09) | 3.33 |
|  | 40 | (2.74 ± 0.08) | 2.5 |
| 150 | 10 | (5.59 ± 0.02) | 10.0 |
|  | 20 | (3.63 ± 0.02) | 5.0 |
|  | 30 | (2.35 ± 0.09) | 3.33 |
|  | 40 | (1.57 ± 0.02) | 2.5 |
| 180 | 10 | (3.17 ± 0.06) | 10.0 |
|  | 20 | (1.49 ± 0.04) | 5.0 |
|  | 30 | (0.81 ± 0.08) | 3.33 |
|  | 40 | (0.40 ± 0.03) | 2.5 |

Figure 4:
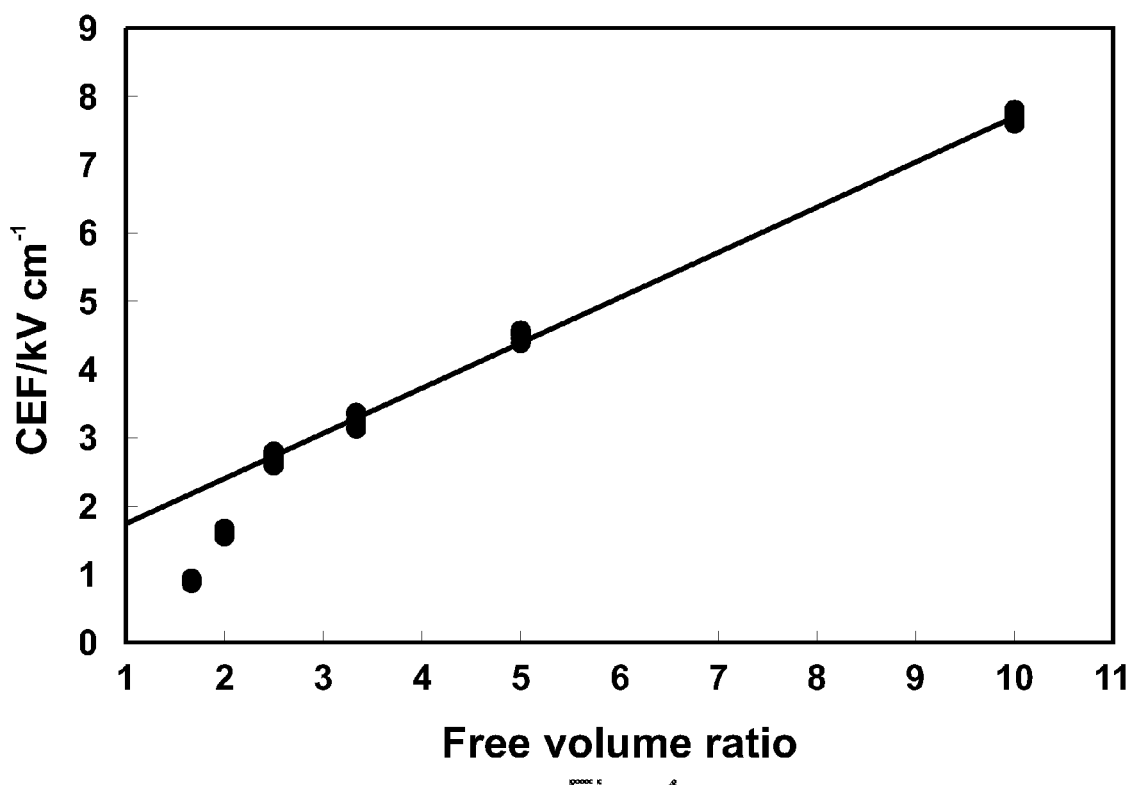
FIG. 4 is a plot of CEF against $1/\phi$.

The observed deviation in the linear relationship, as well as the increased intercept in the plot of CEF against $1/\phi$ in FIG. 4, are explained to be the result of two processes. Firstly, the downward curvature in the CEF plot at low $1/\phi$ (high water content) is most likely the result of reverse emulsion formation. With increasing water loading into the system, a portion of the water is absorbed in the formation of a mixed (or even complex) emulsion. An increase in water external character of the emulsion, will increase conductivity of the emulsion, which could result in a sharp decrease in the observed CEF measurement.

Secondly, the increased intercept in the plot of CEF against $1/\phi$ can be explained by a coalescence-controlled mechanism of demulsification. In this case, the rate of demulsification is not only dependent on the probability of a collision, but also on the energy required to effect coalescence. Although the coalescence-controlled mechanism is the rate-determining step, flocculation is still a prerequisite in the consecutive process (See FIG. 1) and energy required for coalescence is additive to the amount of energy required for flocculation. Hence, the energy required for coalescence will be indicated in the CEF measurement, as a positive deviation above the linear energy requirement for flocculation.

The CEF-value at $V_{1/\phi}=1$, can be determined by extrapolation of the linear portion of a CEF plot against $1/\phi$. This value is a quantitative indication of the barrier to coalescence. A high barrier to coalescence will correspond with a high CEF-value at $V_{1/\phi}=1$. It is believed that this condition approaches a situation of very low oil content and could therefore be expected to behave very similar to a thin film condition.

It is noted that almost all the crude oil blends have a tendency to form less stable emulsions at higher temperatures and that the mechanism of demulsification could change with the temperature at which the emulsion was made up. It appears that emulsions made up at lower temperatures, show more coalescence-controlled behavior (higher barriers to coalescence), than emulsions made up at higher temperatures.

It is believed that emulsions made up at higher temperatures form under less viscous conditions, which can result in the formation of a smaller droplet size distribution and, consequently, a much higher surface area. If the emulsion stability is dependent on natural surfactants in the crude oil, a higher surface area will correspond to lower surfactant concentration at the interface with reduced emulsion stability as a result. However, this might not be a general rule, since it is possible that emulsion stability of other crude oil systems can possibly benefit from a reduction in surfactant concentration at the interface. It is also possible that temperature affects the solubility behavior of the natural surfactants, which will effect the surfactant composition and configuration of chemical composition at the interface. This will result in changes in the stability of emulsions made up at different temperatures, which could be positive or negative, dependent on the crude oil composition.

EXAMPLE 2

Figure 5:
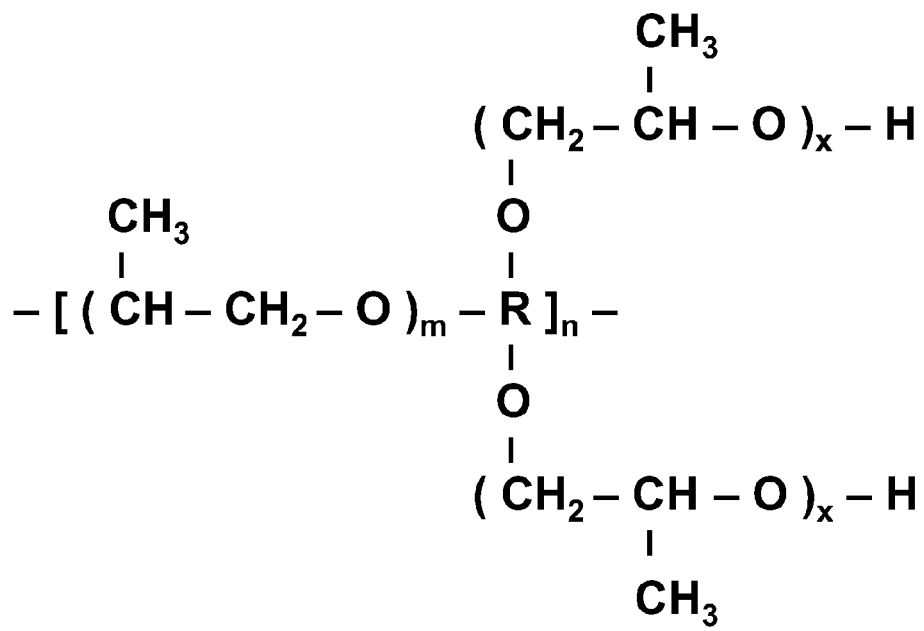
FIG. 5 illustrates the chemical structure of Demulsifier A.

The present invention facilitates evaluation of the effect of a chemical demulsifier on crude oil emulsions using an internal phase ratio variation approach to the CEF technique. One homogeneous crude oil sample from Blend 5 was selected for all experimental work on chemical demulsifiers, since this particular blend showed relatively high resistance to coalescence. A high molecular mass alkoxylate non-ionic polymer, labeled Demulsifier A, was selected and applied as a chemical demulsifier in a series of experiments. The chemical structure of Demulsifier A is graphically presented in FIG. 5.

The effect of this chemical on emulsion stability was evaluated with application of the CEF method and procedure of the present invention. Crude oil emulsions were made up in a series with varying water content. Each emulsion series was subsequently treated with the chemical demulsifier at at a different concentration. The value of $1/\phi$ was calculated from the actual experimental volumes of oil and water used to make up the emulsions. The results from this series of experiments are summarized in Table 3. The data is graphically presented in FIG. 6 as a plot of observed CEF, as a function of demulsifier concentration, for each internal phase ratio (IPR) applied. The observed relationship between CEF and $1/\phi$ for each emulsion series, characterized by a given demulsifier concentration, is graphically presented in FIG. 7.

Figure 6:
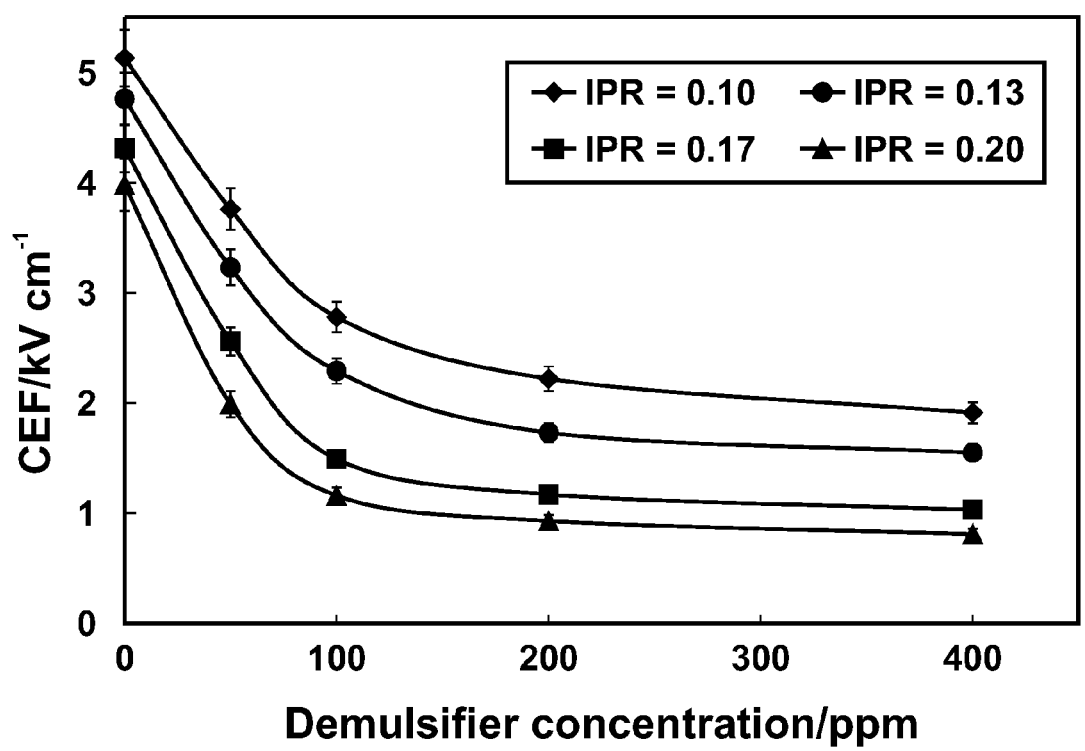
FIG. 6 is a plot of CEF as a function of chemical demulsifier concentration.

The effect of Demulsifier A on the stability of emulsions from Blend 5 is clearly illustrated in FIG. 6. Demulsifier A seems to be more effective in emulsions with higher water content. The amount of energy required to break an emulsion with a water content of 20% (IPR=0.20) is reduced by almost 50% in the presence of demulsifier A at a concentration of 50 ppm. However, the performance of this particular demulsifier levels off around 200 ppm, with very little change in destabilization effect above 200 ppm. At these concentration conditions, the amount of energy required to break the same emulsion is almost four times lower than in the absence of the demulsifier.

TABLE 3

CEF data for water-in-oil emulsions made up with varying water content and treated with various concentrations of Demulsifier A.

| [Demulsifier A]/ ppm | Water content/% | CEF/ kV cm−1 | $1/\phi$ |
| --- | --- | --- | --- |
| 0 | 10.14 | (5.10 ± 0.1) | 9.86 |
|  | 12.70 | (4.76 ± 0.09) | 7.87 |
|  | 16.93 | (4.31 ± 0.07) | 5.91 |
|  | 20.36 | (3.98 ± 0.07) | 4.91 |
| 50 | 10.14 | (3.76 ± 0.07) | 9.86 |
|  | 12.70 | (3.23 ± 0.08) | 7.87 |
|  | 16.93 | (2.56 ± 0.04) | 5.91 |
|  | 20.36 | (2.0 ± 0.1) | 4.91 |
| 100 | 10.14 | (2.8 ± 0.1) | 9.86 |
|  | 12.70 | (2.3 ± 0.1) | 7.87 |
|  | 16.93 | (1.49 ± 0.09) | 5.91 |
|  | 20.36 | (1.16 ± 0.05) | 4.91 |
| 200 | 10.14 | (2.2 ± 0.1) | 9.86 |
|  | 12.70 | (1.73 ± 0.05) | 7.87 |
|  | 16.93 | (1.17 ± 0.06) | 5.91 |
|  | 20.36 | (0.93 ± 0.03) | 4.91 |
| 400 | 10.14 | (1.91 ± 0.06) | 9.86 |
|  | 12.70 | (1.55 ± 0.09) | 7.87 |
|  | 16.93 | (1.03 ± 0.06) | 5.91 |
|  | 20.36 | (0.81 ± 0.06) | 4.91 |

Figure 7:
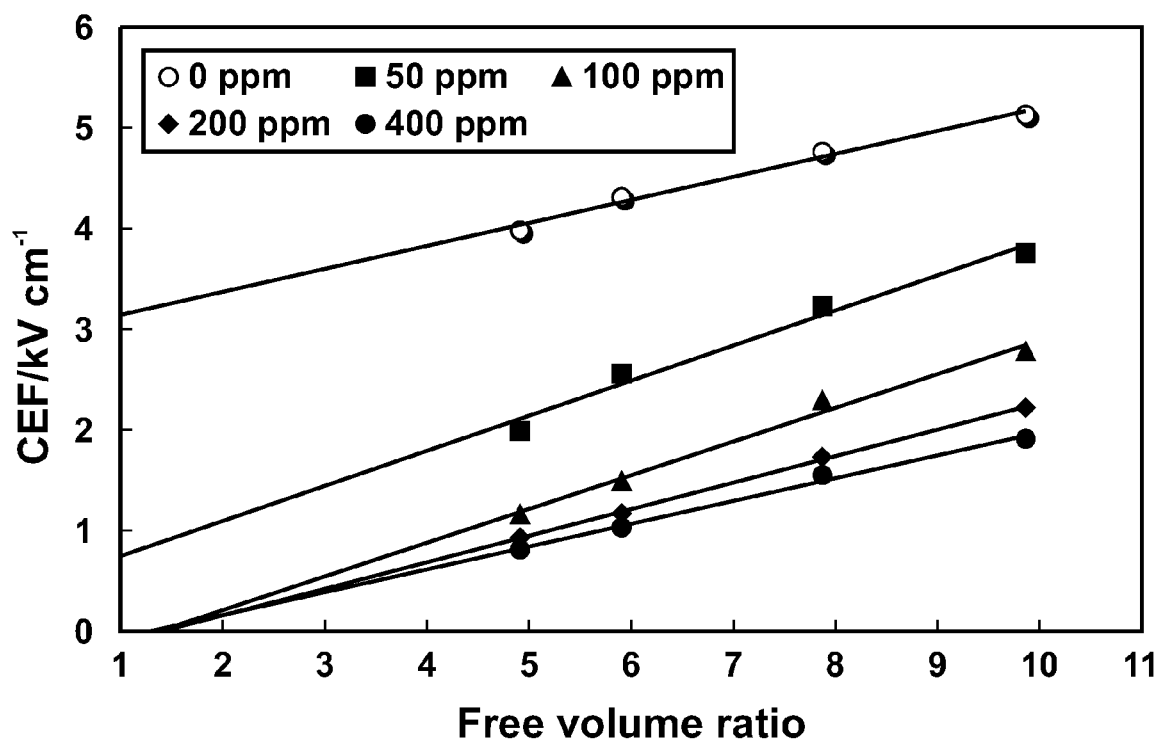
FIG. 7 is a plot of CEF against $1/\phi$.

FIG. 7 illustrates the mechanism of emulsion stabilization and the mechanism of chemical demulsifier function. Emulsions made up from this particular crude oil blend show a high barrier to coalescence as indicated by the high extrapolated CEF value at $V_{1/\phi}=1$. It is clear that the chemical demulsifier destabilizes the emulsion by effective reduction of this barrier to coalescence. However, the slope of the plot in FIG. 7 appears to show a slight increase in the presence of the demulsifier.

The effect of the chemical demulsifier on the crude oil emulsion stability can be evaluated in terms of the individual flocculation and coalescence components of the emulsion stabilization mechanism. Furthermore, the relative energy involved in the emulsion breaking process can be calculated by expressing the experimental data as normalized values with respect to the untreated (control) crude oil emulsion. It is thus possible to calculate the relative amount of energy required (compared to the untreated emulsion or control) for the flocculation as well as coalescence processes involved in demulsification by any chemical demulsifier.

Figure 8:
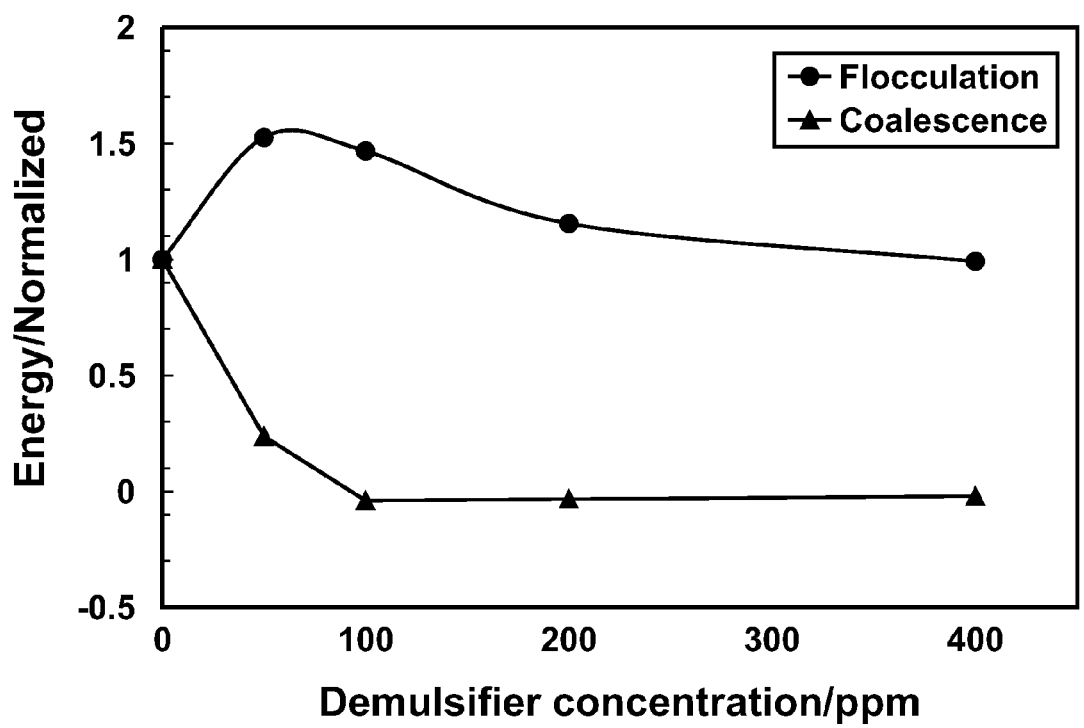
FIG. 8 is a plot of normalized energy as a function of Demulsifier A concentration for both the flocculation process and the coalescence process

The slope of the plot in FIG. 7, as well as the extrapolated CEF value at $V_{1/\phi}=1$, is calculated from the experimental data in Table 3, for each of the five emulsion series representing a control and four demulsifier concentrations. The results are expressed as normalized values with respect to the control, i.e., the crude oil emulsion without the chemical demulsifier. FIG. 8 illustrates the effect of the chemical demulsifier as a plot of normalized energy as a function of Demulsifier A concentration for both the flocculation process and the coalescence process. The relative amount of energy involved in demulsification can be presented as a normalized plot of the flocculation behavior of the emulsion (from the slopes in FIG. 7) and the coalescence behavior (from the extrapolated CEF values at $V_{FR}=1$) as a function of the concentration of the chemical demulsifier.

It is noted that the extrapolated CEF-values at $V_{1/\phi}=1$, in FIG. 7, tend to be slightly negative. Moisture analysis of the crude oil sample, by Karl Fischer titration showed only trace amounts of water present. However, the extrapolated CEF-value is sensitive to the amount of water present and any additional water will shift the extrapolated CEF-value lower. The presence of water in the original crude oil sample is considered to be a contributing factor to the small shift in the extrapolated CEF-value in FIG. 7.

FIG. 8 shows that the chemical demulsifier actually stabilizes the emulsion at lower concentrations, by increasing the amount of energy required for flocculation by more than 50%. However, the same chemical drastically reduces the energy required for coalescence, to have an overall destabilization effect on the emulsion. At demulsifier concentrations above 100 ppm, the barrier to coalescence is almost completely removed. The energy required for flocculation gradually decreases at higher demulsifier concentrations to an energy level typical of the crude oil without demulsifier present. The chemical appears to be reluctant in reducing the energy required for flocculation.

EXAMPLE 3

Figure 9:
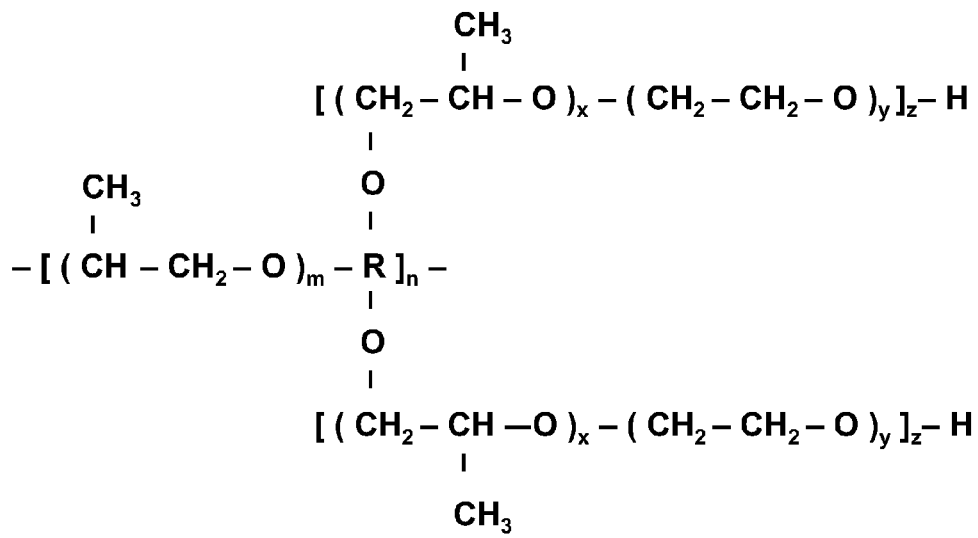
FIG. 9 illustrates the chemical structure of Demulsifier B.

Another demulsifier is selected from the same chemical family to evaluate the ability of the internal phase ratio-based CEF technique to distinguish between the effects of these two related chemical structures on emulsion stability. A non-ionic alkoxylate polymer, similar to Demulsifier A, is selected and applied as Demulsifier B. Demulsifier B contained an additional polyethylene oxide block in its branch, with an increase of approximately 20% in its molecular mass. The chemical structure of Demulsifier B is graphically presented in FIG. 9.

The effect of Demulsifier B on the stability of emulsions was evaluated using the internal phase ratio-based CEF method and procedure of Example 2. Crude oil emulsions were made up in a series with varying water content. Each emulsion series was subsequently treated with Demulsifier B at a different concentration. To improve the accuracy of the results, internal phase volume ratios were calculated from the actual experimental volumes of oil and water used to make up the emulsions. The observed results from this series of experiments are summarized in Table 4. The data in Table 4 is compared with observations from similar experiments with Demulsifier A.

Figure 10:
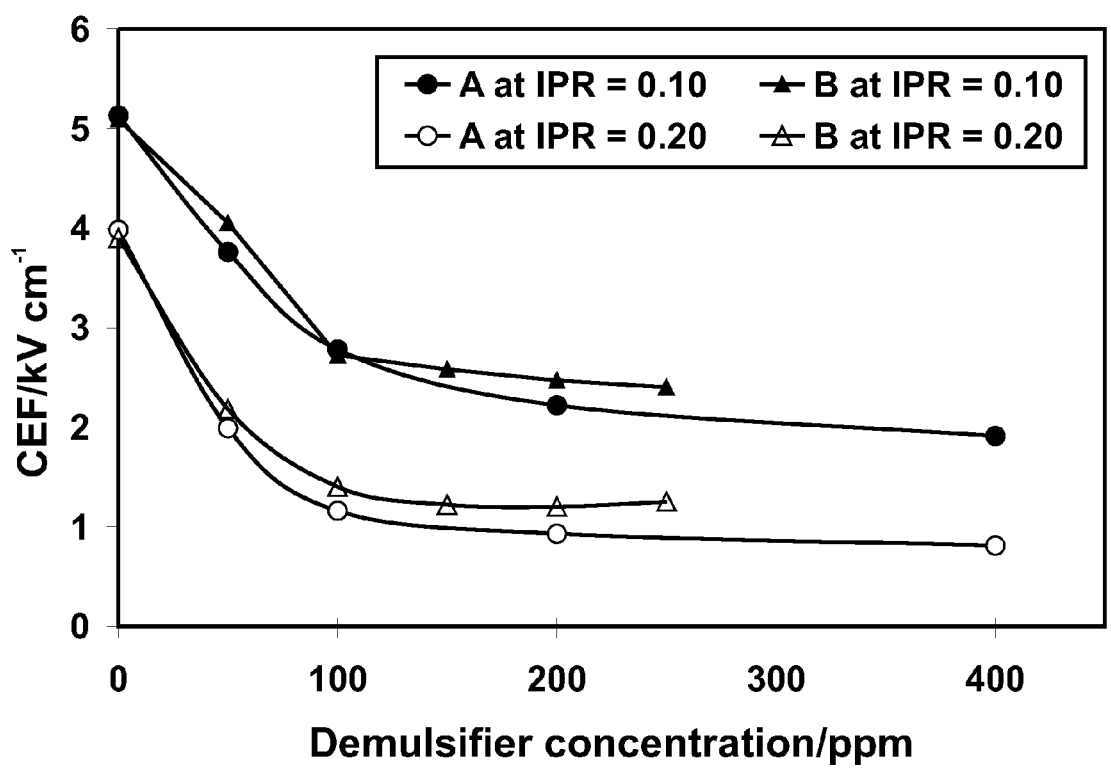
FIG. 10 is a plot of CEF as a function of demulsifier concentration for both Demulsifier A and Demulsifier B.

The results are graphically presented in FIG. 10 as a plot of observed CEF as a function of demulsifier concentration for both Demulsifier A and Demulsifier B. Experimental results for both the highest and lowest internal phase volume ratio (IPR), $\phi=0.10$ and $\phi=0.20$, are indicated in FIG. 10 to illustrate the typical trend in the comparison. The observed linear relationship between CEF and $1/\phi$, for each demulsifier concentration applied, is graphically presented in FIG. 11 as listed in Table 4.

TABLE 4

CEF data collected for water-in-oil emulsions made up with varying water content and treated with various concentrations of Demulsifier B.

| [Chemical]/ ppm | Water content/% | CEF/ kV cm−1 | Free volume ratio |
|---|---|---|---|
| 0 | 10.07 | (5.09 ± 0.09) | 9.93 |
|  | 12.66 | (4.59 ± 0.07) | 7.90 |
|  | 17.40 | (4.07 ± 0.06) | 5.75 |
|  | 20.31 | (3.90 ± 0.04) | 4.92 |
| 50 | 10.07 | (4.1 ± 0.1) | 9.93 |
|  | 12.66 | (3.5 ± 0.1) | 7.90 |
|  | 17.40 | (2.61 ± 0.08) | 5.75 |
|  | 20.31 | (2.18 ± 0.07) | 4.92 |
| 100 | 10.07 | (2.72 ± 0.08) | 9.93 |
|  | 12.66 | (2.25 ± 0.07) | 7.90 |
|  | 17.40 | (1.80 ± 0.05) | 5.75 |
|  | 20.31 | (1.40 ± 0.06) | 4.92 |
| 150 | 10.07 | (2.58 ± 0.08) | 9.93 |
|  | 12.66 | (1.98 ± 0.04) | 7.90 |
|  | 17.40 | (1.45 ± 0.05) | 5.75 |
|  | 20.31 | (1.22 ± 0.06) | 4.92 |
| 200 | 10.07 | (2.5 ± 0.1) | 9.93 |
|  | 12.66 | (1.93 ± 0.08) | 7.90 |

TABLE 4-continued

CEF data collected for water-in-oil emulsions made up with varying water content and treated with various concentrations of Demulsifier B.

| [Chemical]/ ppm | Water content/% | CEF/ kV cm−1 | Free volume ratio |
|---|---|---|---|
|  | 17.40 | (1.43 ± 0.05) | 5.75 |
|  | 20.31 | (1.20 ± 0.04) | 4.92 |
| 250 | 10.07 | (2.4 ± 0.1) | 9.93 |
|  | 12.66 | (1.95 ± 0.04) | 7.90 |
|  | 17.40 | (1.47 ± 0.05) | 5.75 |
|  | 20.31 | (1.25 ± 0.06) | 4.92 |

The results shown in FIG. 10 indicate that the internal phase ratio-based CEF technique, as well as the experimental procedure followed, allow suitable sensitivity for quantitative structure activity relationship studies. Demulsifier B appears to be less effective than Demulsifier A, in destabilizing the emulsion. Demulsifier B also shows a tendency to reach a maximum effect below 200 ppm, above which an increase in demulsifier concentration leads to an increase in emulsion stability. This phenomenon is well known for demulsifiers and commonly referred to as "over treat."

Figure 11:
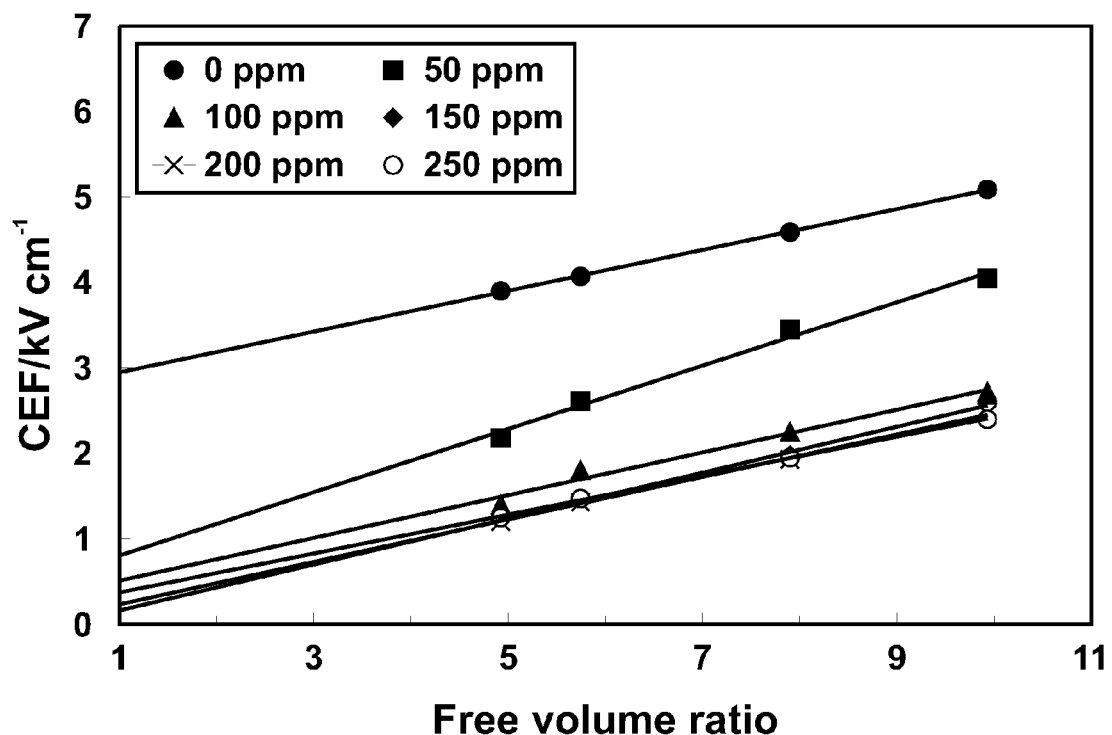
FIG. 11 is a plot of CEF against $1/\phi$.

The slope of the plot in FIG. 11 as well as the extrapolated CEF value at $V_{1/\phi}=1$ is calculated from the experimental data in Table 4. The results for Demulsifier B are compared with the results obtained for Demulsifier A and summarized in Table 5, for each of the different demulsifier concentrations applied. The values in Table 5 are expressed as normalized values with respect to the crude oil emulsion (the control without demulsifier), for each demulsifier concentration condition, as an indication of the relative amount of energy involved in the mechanism of demulsification.

TABLE 5

Comparison of observed slope and extrapolated CEF values, from experiments with chemical demulsifiers A and B.

| Dem | [Dem]/ppm | Slope | $V_{FR} = 1$ |
|---|---|---|---|
| A | 0 | (0.23 ± 0.02) | (3.1 ± 0.1) |
|  | 50 | (0.35 ± 0.04) | (0.8 ± 0.3) |
|  | 100 | (0.33 ± 0.03) | (−0.1 ± 0.2) |
|  | 200 | (0.264 ± 0.006) | (−0.11 ± 0.04) |
|  | 400 | (0.23 ± 0.01) | (−0.1 ± 0.1) |
| B | 0 | (0.239 ± 0.004) | (2.95 ± 0.03) |
|  | 50 | (0.37 ± 0.03) | (0.8 ± 0.2) |
|  | 100 | (0.25 ± 0.03) | (0.5 ± 0.2) |
|  | 150 | (0.269 ± 0.008) | (0.16 ± 0.06) |
|  | 200 | (0.249 ± 0.005) | (0.23 ± 0.04) |
|  | 250 | (0.228 ± 0.004) | (0.37 ± 0.03) |

Figure 12:
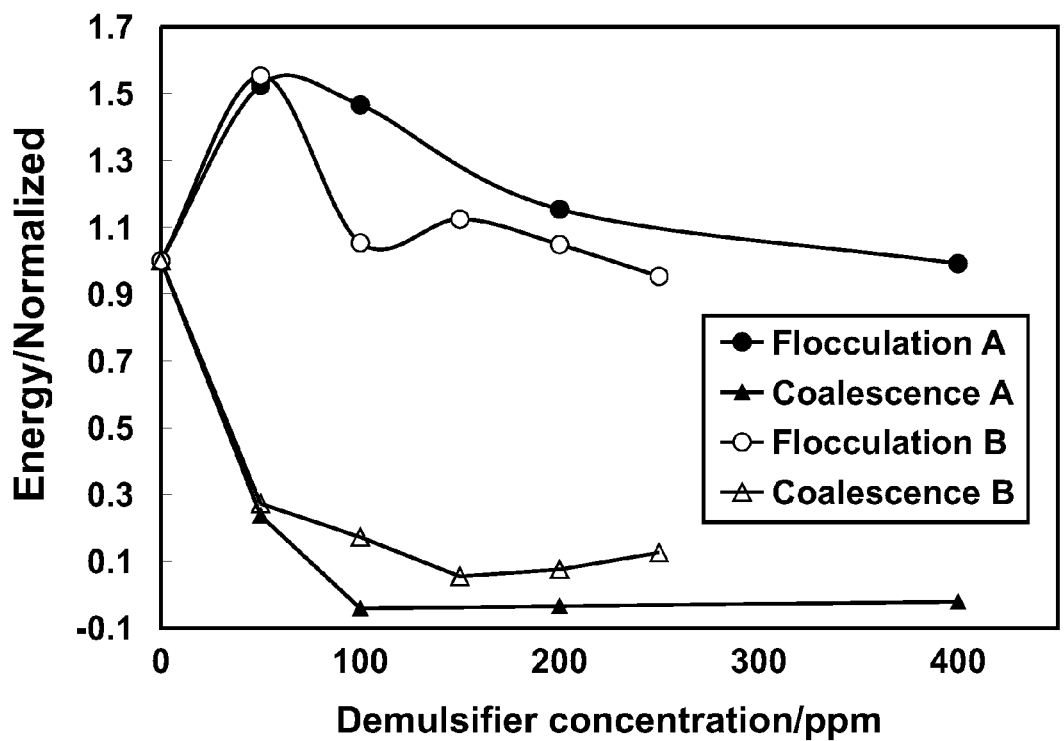
FIG. 12 is a graphical comparison of the relative energy involved in the flocculation as well as coalescence steps of demulsification with respect to both the two chemical demulsifiers.

FIG. 12 shows a graphical comparison of the relative energy involved in the flocculation as well as coalescence steps of demulsification with respect to both the two chemical demulsifiers.

The differences as well as similarities in the effect of the two chemical demulsifiers are illustrated in FIG. 12. Both demulsifiers behave very similar up to a concentration of 50 ppm, where an emulsion stabilization effect with respect to flocculation is offset by a larger destabilization effect in terms of coalescence. However, Demulsifier B shows a slightly reduced ability to lower the energy requirement for coalescence, compared to Demulsifier A at concentrations above 50 ppm. Furthermore, Demulsifier B shows an optimum performance in terms of coalescence at 150 ppm, with a decreasing ability to affect coalescence above 150 ppm. In contrast, Demulsifier A shows no indication of an of an optimum or "over treat" condition, even for the much higher concentration range. Considering flocculation effects, Demulsifier B shows ability to improve flocculation at higher concentrations, where Demulsifier A seems to have very little effect at higher concentrations, although the stabilization effect tends to disappear.

A particular set of experimental data showed a prominent zero CEF at an extrapolated inverse internal phase ratio (1/IPR) of ~1.4. This observation is in contradiction to the earlier hypothesis that the Critical Electric Field is expected to approach zero as the internal phase ratio approach unity (1/IPR=1). The observed behavior was connected to Kepler's conjecture and the much postponed proof by Thomas Hales, that the face centered cubic packing (fcc) and the hexagonal close packing (hcp) are the most dense packing density possible for sphere packing. According to the theory, the packing density of congruent spheres in three dimensions is never greater than $\pi/\sqrt{18}=0.7405$ and the application of this number to the CEF problem implies that a droplet packing at maximum density (from where coalescence can proceed) will be equivalent to an inverse internal phase ratio (1/IPR) of $1/0.7405=1.350$ which is in agreement with the experimental observation. It appears that the coalescence coefficient can be more accurately calculated as $C_c=1.35*C_f+I$, where $C_f$ is the slope and I the intercept from the observed relationship between CEF and 1/IPR (or $IPR^{-1}$), which is given as $CEF=C_f*IPR^{-1}+I$. (In the original provisional patent, $C_c$ is calculated at the sum of $C_f$ and I).

EXAMPLE 4

The IPR-CEF technique was originally developed for application to water-in-oil emulsions encountered in the oil field. However, it is believed that the "IPR"-theory can be applicable to other types of emulsions (such as oil-in-water, etc.), using another type of demulsification and or measuring technique.

Figure 13:
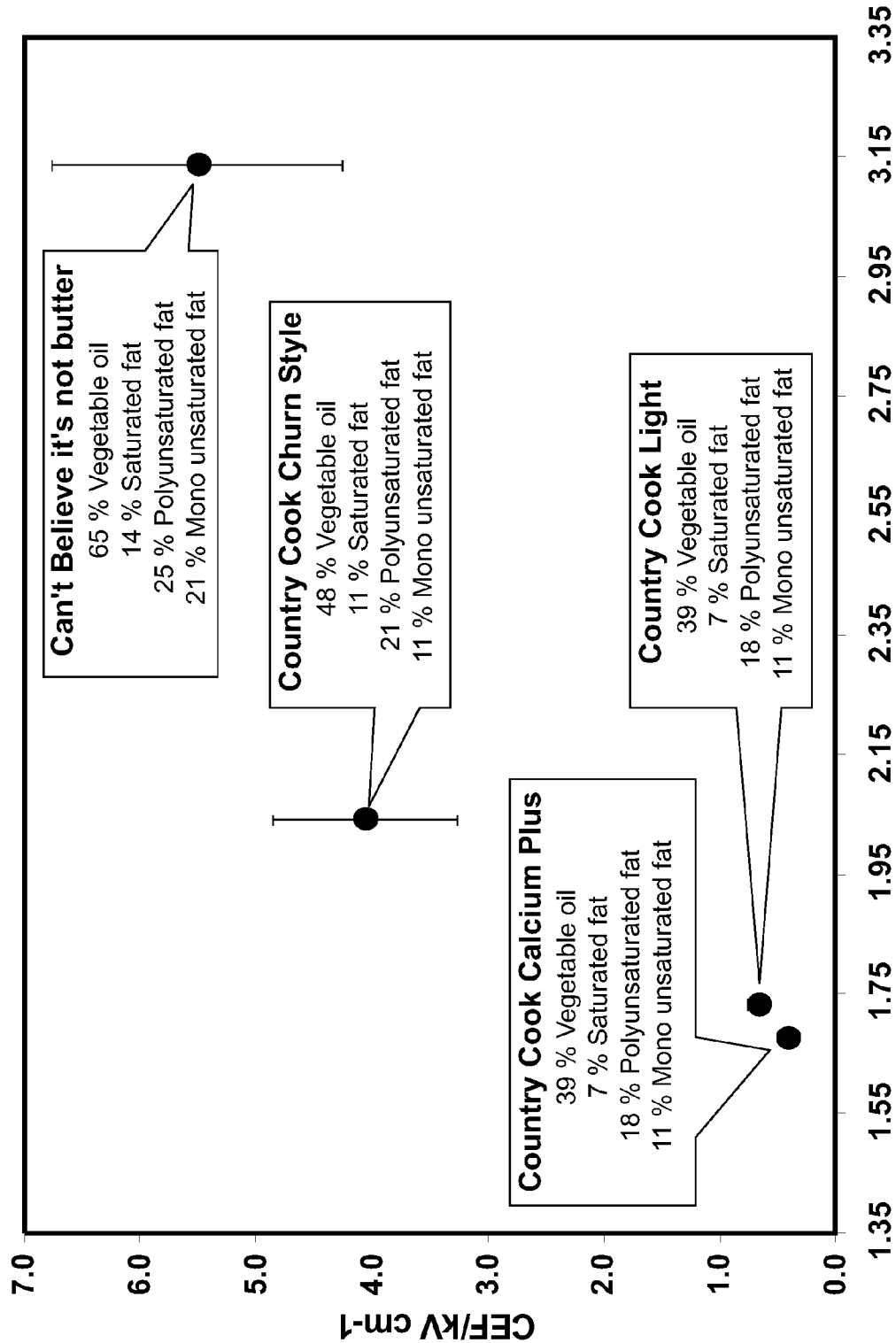
FIG. 13 is an IPR-CEF plot observed for different margarine samples.

To investigate possible application of the IPR-CEF technique in other areas of interest, the stability of commercially available margarines were evaluated by the IPR-CEF method as a typical illustration of application to the food industry. FIG. 13 shows an IPR-CEF plot of experimental results for four different margarines. The water content of each of the margarine samples was determined by melting and subsequent centrifugation. The compositional information is printed as supplied on the individual product labels.

FIG. 13 is an IPR-CEF plot observed for different margarine samples. Although the emulsions differ in composition of the oil phase and most likely with substantial differences in the conditions of production, it was noted that the trend was typical of the IPR-CEF relationship where an increase in inverse of the internal phase ratio is associated with an increase in the Critical Electric Field (CEF) measurement. The large experimental error is attributed to the CEF electrode configuration which is not ideal for handling the paste consistency of the sample. This problem can be solved with a more suitable design of the sampling cell where the sample is completely replaced between each measurement.

To show the span of application of the IPR-CEF technique, the results for margarines in FIG. 13 was compared to IPR-CEF results obtained on emulsions based on diluted coker feed bitumen, which is typical of crude oil emulsions encountered in the oil and gas industry. The comparison is shown in FIG. 14A.

Figure 14A:
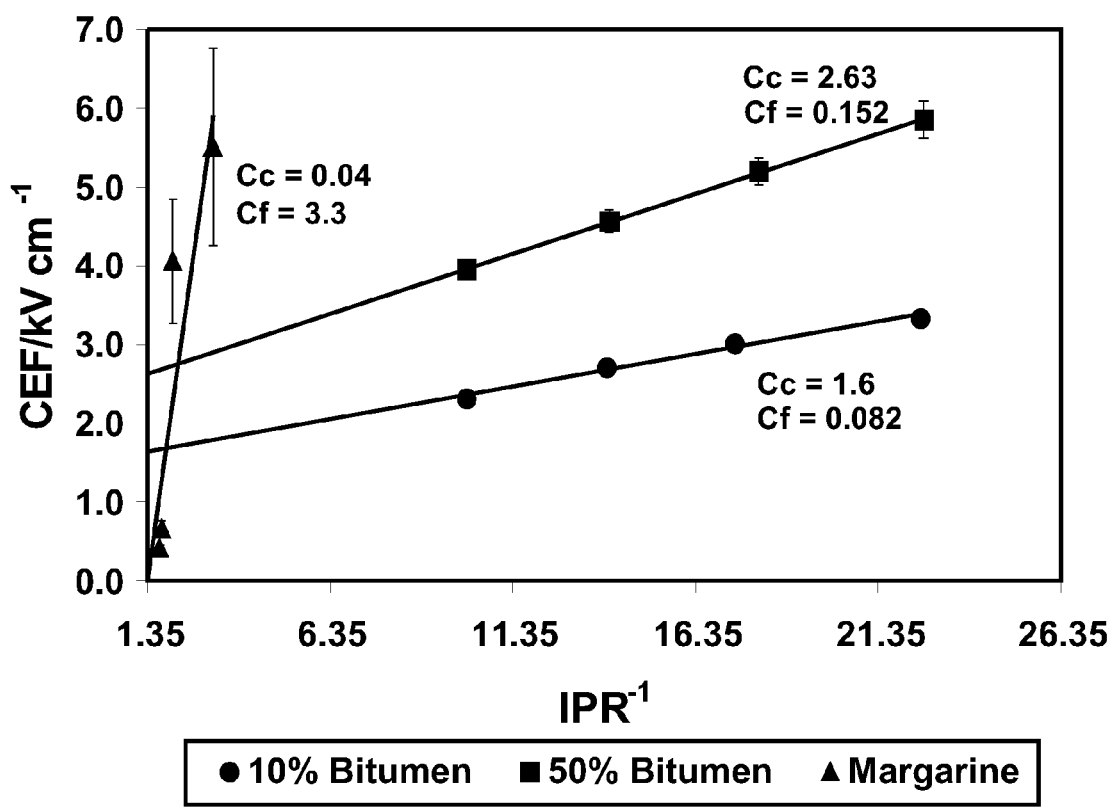
FIG. 14A is an IPR-CEF plot comparing results from two different industries.

FIG. 14A is an IPR-CEF plot comparing results from two different industries. FIG. 14A shows the IPR-CEF results for two different concentrations of coker feed bitumen in toluene, compared to the results for four different margarines. Although the margarine samples can not really be comparable in the same group, the relationship is striking when compared to the bitumen based emulsions. This is a fine illustration of how the IPR-CEF technique can reveal the mechanism of emulsion stabilization. The bitumen emulsions, with much higher coalescence coefficients are mostly stabilized by a barrier to coalescence, while the margarine emulsions are stabilized by a barrier to flocculation—most likely due to the high viscosity of the cooled down bulk phase. It is very encouraging to note that the CEF approach zero close to the theoretical value of IPR=1.35.

EXAMPLE 5

The possible application of the IPR-CEF technique was investigated in some conceptual work in a refinery-type process. The demulsifier was turned off for reasonable periods of time as well as vary the wash water content between 1.2% and 7%, during the production of ~50,000 barrels per day. We were provided with a ¼" sampling line and two valves on the outlet of the feed pump to the electrostatic desalter. We had several objectives with this work: The ability to get a reading in the practical range (Electric field strength of less than 12 kV $cm^{-1}$) represented our first level of success. The hope to have a precision better than 10%, were surpassed with the observed standard deviation of ~3%. The question if the effect of the demulsifier will be noticeable with the CEF technique, was answered as a third level of success. Finally, the linear relationship between CEF data and $IPR^{-1}$ (inverse of the internal phase ratio) was confirmed, implying that the mechanism of emulsion stability (in terms of flocculation and coalescence components) can be quantified by IPR-CEF in real time, on-line, application at refineries.

Figure 14B:
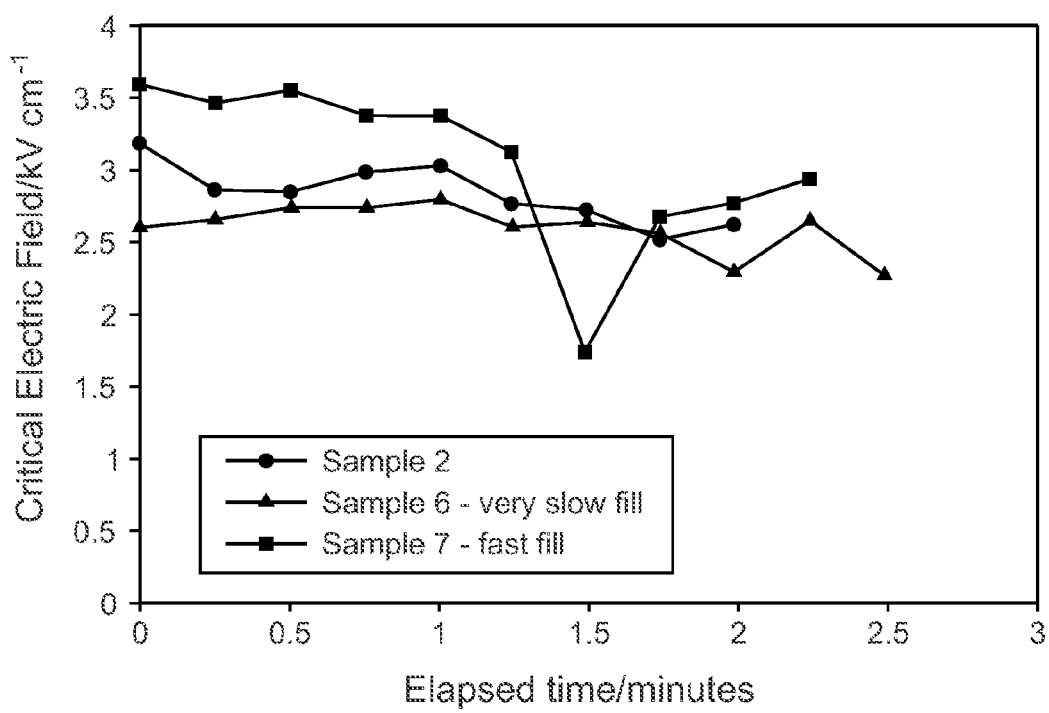
FIG. 14B shows the CEF measurements from a refinery.

A typical CEF data from the LaGloria refinery is shown in FIG. 14B. It was discovered that the stability of the collected sample also depended on the rate at which the sample was collected. This is understandable, since the emulsion is released from a pressure of 250 psig, through the partially opened orifice of a ¼" valve.

FIG. 14B shows typical CEF data collected on emulsion samples taken at various rates. It was noted that the emulsion stability decreased slightly during the first few minutes after sampling. Some sporadic excursions were seen, mostly with errors or standard deviations well above 10%, as shown in FIG. 14B. The data set showed a standard deviation below 3%, once the few erratic data points had been removed.

Figure 14C:
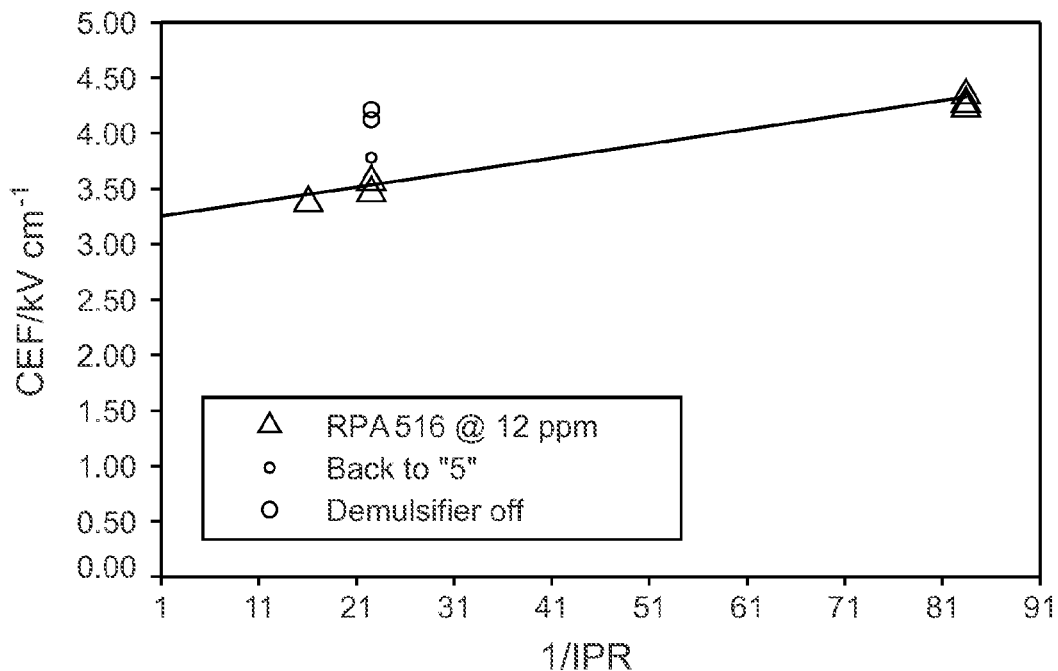
FIG. 14C shows the results from an IPR-CEF study on the refinery.

Results from an IPR-CEF study on the refinery are shown in FIG. 14C. The water content of the desalter feed stream was set at three different levels. The CEF data in FIG. 14C was collected in a series of experiments, which started at 3.28% water content, then increased to 4.55% and followed by another increase to 6.40%. Thereafter, the feed stream composition was returned to 4.55%, making frequent CEF measurements. The demulsifier RPA 516, was turned off, with CEF data collected at elapsed time intervals of 10, 15 and 18 minutes, before the original operational conditions were re-established. Jim Ewen, our Ashland partner at LaGloria, later reported that the setting of 3.28% actually represent a water content of 1.2% and reasoned that the valve closes earlier than expected in the calibration. The data in FIG. 14C include this correction made for the 3.28% data point only and gives the expected linear relationship. The high intercept (high coalescence coefficient) and low slope (low flocculation coefficient) in FIG. 14C suggest that this emulsion is particularly difficult to coalesce, with a relative low barrier to flocculation.

The effect of demulsifier RPA 516 might appear small in FIG. 14C, lowering CEF from 4.2 kV cm$^{-1}$ to 3.6 kV cm$^{-1}$ (a reduction of ~14%), but it is dosed at a concentration of only 12 ppm, which seems to be sufficient for the required effect. However, it is important that we can see the effect of the demulsifier and distinguish it from the effect of water content, with application of the IPR-CEF theory.

The experimental results and observations from this study confirm the linear relationship between CEF measurement and the corresponding 1/φ as proposed. This relationship is confirmed by various crude oil emulsions, made up at different temperatures, by different procedures, with or without chemical treatment at various levels.

It is believed that the mechanism of emulsion stabilization is revealed in terms of the flocculation as well as coalescence components according to the internal phase ratio based CEF-technique of the present invention. The information provided by this method is very useful in the understanding of the mechanism of chemical demulsifier action on a crude oil emulsion, by revealing the effect of the chemical on both, the flocculation as well as the coalescence behavior of the emulsion.

The invention provides a new internal phase volume ratio-based CEF technique that reveals the mechanism of emulsion stabilization of water in crude oil emulsions. This technique makes it possible to determine the nature of emulsion stability in terms of flocculation and coalescence behavior. The same technique is applied to reveal the mechanism of chemical demulsifier function in the destabilization of a crude oil emulsion. It is believed that the insights gained from application of this technique will be of significant benefit to quantitative structure activity relationship studies. Both the mechanism of emulsion stabilization as well as the mechanism of chemical demulsifier function is reveled by the application of the method developed in the study.

On-line applications during production processes include process monitoring, alarm functions, plant optimization and automatic operation control which could include process control as well as additive addition monitoring and control.

The IPR-CEF technique (and IPR-"Other technique") find application in various industries where emulsion stability is of importance, such as the food, road construction, paint, cosmetic, pharmaceutical, etc., industries.

Another important aspect to acknowledge is that a CEF measurement gives an indication of emulsion stability at a given stage during the demulsification process. If a CEF measurement is made directly following the formation of an emulsion, the measurement will reflect the stability of a first generation of droplets. If the first generation droplets are allowed time to coalesce to form a second generation, or a third, etc., the total surface area of the newly formed droplets is reduced. A reduced surface area can result in an increase in concentration of interfacial or surface-active material which can affect the stability of the newly formed emulsion. Thus for a more complete picture of the stability of an emulsion system, CEF measurements must also be made during the progression of a demulsification process.

As an alternative or in combination with IPR-CEF, it is possible to apply a CEF based technique which we call "differential CEF". This technique is of particular benefit where emulsion stability or water content fluctuates. The effect of chemical addition or process conditions between two locations of CEF measurement can then be distinguished from the fluctuating signal by subtracting the two measurements. The information in the "differential signal" will depend on the location of the individual CEF measurements, which can include more than two locations with multiple resultant signals, each revealing a different aspect of the process. Measurements can be made simultaneously or with specific time lag between comparable measurements. There are no limits to the number of locations of CEF measurements or time differences between related measurements.

Emulsion System Analysis Using IPR-CEF Techniques

Figure 15:
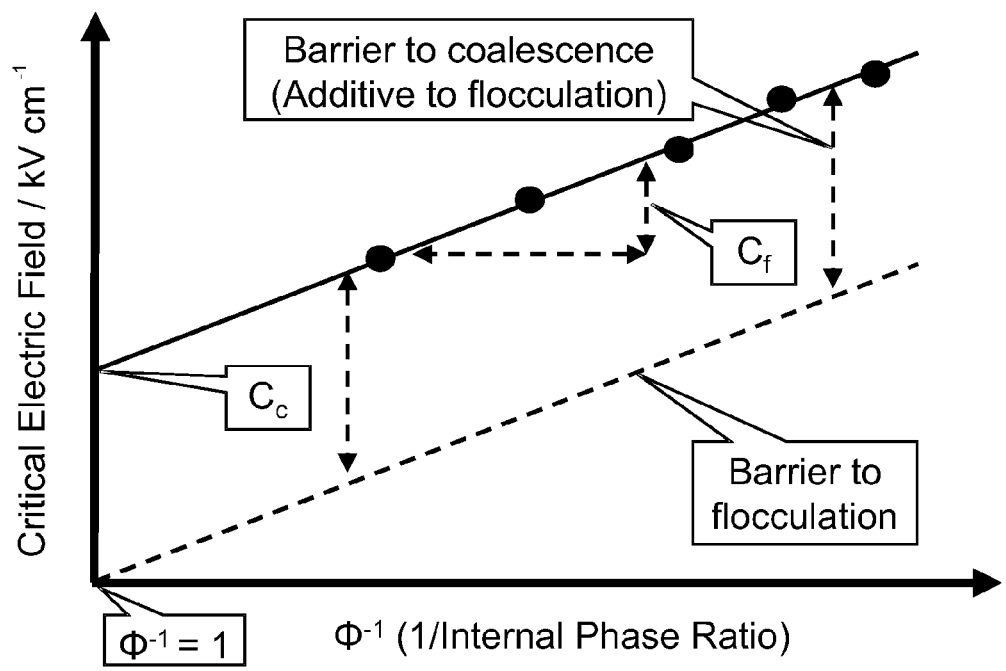
FIG. 15 provides a graphical representation of the IPR-CEF Technique.

It is believed that the observed slope of this relationship, gives a quantitative indication of the relative amount of energy required to flocculate the droplets. FIG. 15 provides a graphical representation of the IPR-CEF Technique. Thus, equation (8) can be written as;

$$CEF = C_f \phi^{-1} + c \quad (9)$$

Where the flocculation constant, $C_f$, is a relative indication of the tendency to flocculate, while the intercept, c, is used to calculate the coalescence constant, $C_c$, as an indication of the relative amount of energy required for coalescence of flocculated droplets, with;

$$C_c = C_f + c \quad (10)$$

A high flocculation constant will imply a large barrier to flocculation and a high coalescence constant will be associated with a large barrier to coalescence. It is believed that this method can provide insight related to the mechanism of emulsion stabilization as well as quantitative information on the mechanism of demulsification by chemical treatment.

EXAMPLE 6

The experimental work was very explorative, with the primary aim to evaluate the validity of the proposed relationship between CEF data and the corresponding internal phase ratio, under various conditions. A number of water-in-oil emulsions were made up from three different Offshore China crude oil samples, with distilled water, synthetic brine and saline solutions as the aqueous phase. The different methods of agitation included a Rushton type paddle at 3,000 RPM for 5 minutes and a constant speed blender at 12,000 RPM for 1 minute, with temperature variation between 21 and 82° C.

Critical Electric Field data were calculated from measurements made with a Model ESM-30B electric stability tester, which is traditionally used for the evaluation of drilling mud. The instrument is configured as a submersible probe with parallel electrodes. A potential-difference is ramped up between two parallel plates with an AC signal of 340 Hz, at a rate of 150 V s$^{-1}$, to a maximum of 2 kV, which represents an upper limit of 12.6 kV cm$^{-1}$ for the electric field applied.

Some specific experimental work was done to evaluate the relevance of the IPR-CEF technique in research related to the effect of aqueous phase composition on the mechanism of emulsion stabilization. For this purpose, emulsions were made up with China C crude oil and sodium chloride solutions, at concentrations from 0 to 20 mass %. These emulsions were made up with a constant speed blender at 21° C.

A brief investigation of chemical demulsifier effect was included in the experiments. Emulsions were made up with China B crude oil and synthetic brine, using a constant speed blender at 21° C. All emulsions were subsequently treated with two typical chemical demulsifiers of very similar chemical structure. Demulsifier A is a high molecular mass complex polypropylene glycol, with a comb-type configuration. Demulsifier B is very similar, but contains ethylene oxide in the pendant chain to form a polypropylene glycol-ethylene glycol co-polymer, with 20% increase in molecular mass.

Figure 16:
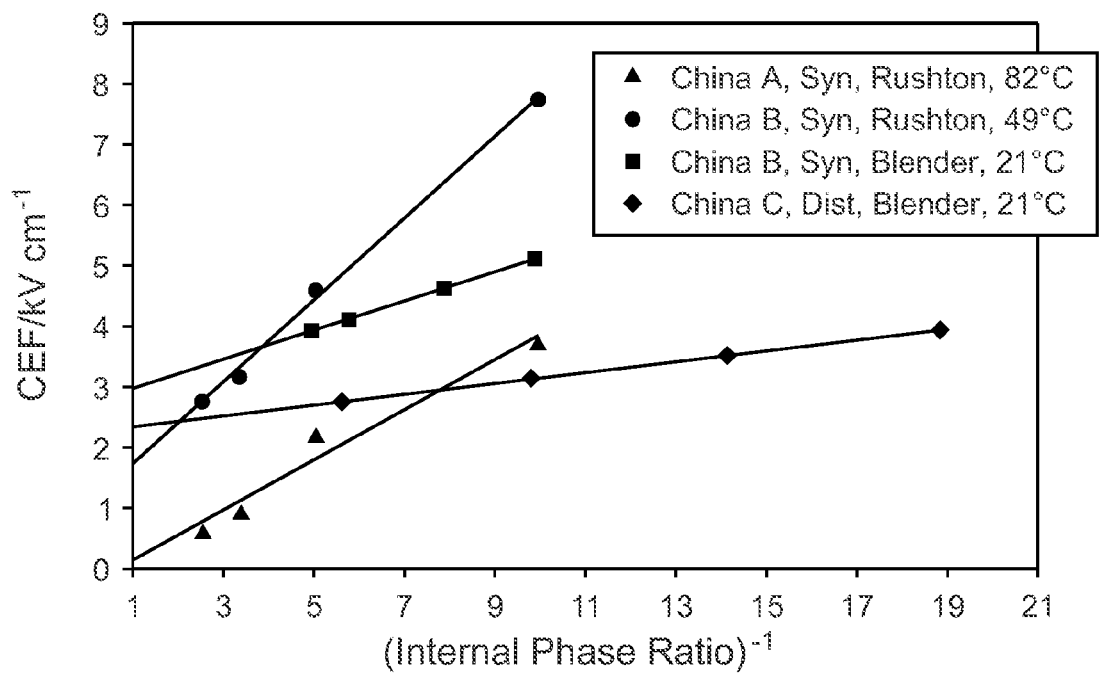
FIG. 16 is an IPR-CEF plot of emulsions made form three different crude oil samples, with both synthetic brine and distilled water, in two different modes of agitation, at three different temperatures.

CEF measurements were found to be directly proportional to the inverse of the internal phase ratio, as suggested by equation (8), in all configurations of the investigation. FIG. 16 shows typical results from a diverse number of experiments. The data in FIG. 16 was collected by CEF measurements on emulsions made form three different crude oil samples, China A, China B and China C, with both synthetic brine (Syn) and distilled water (Dist), in two different modes of agitation, at three different temperatures. The proposed linear relationship between CEF and $\phi^{-1}$ was found to be valid for the data shown in FIG. 16, as well as all other cases investigated. Some deviation from linearity was found in a few cases of low $\phi^{-1}$ (high water content), but all of the observed deviation was related to reverse emulsion formation with water as the external phase. CEF data collected on emulsions made up with the Rushton type paddle showed higher experimental error than those made up by the constant speed blender. The flocculation coefficient, $C_f$, as well as the coalescence coefficient, $C_c$, derived from the IPR-CEF relationship, offer significant insight with reference to the mechanism of emulsion stabilization of a particular water-in-oil emulsion system. It is believed that the IPR-CEF technique could be valuable in research related to the effects of both crude oil and brine composition or properties, emulsification conditions and even chemical additives, on the mechanism of emulsion stability or destabilization.

Figure 17A:
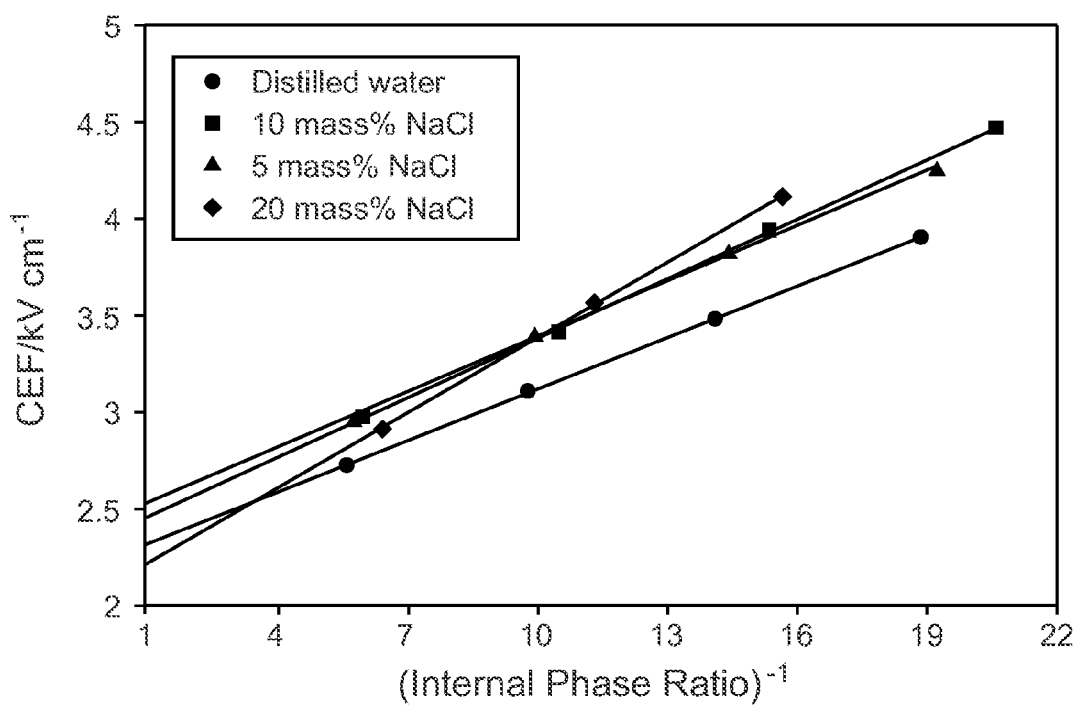
FIG. 17A shows the IPR-CEF relationships observed at different NaCl-concentrations of an aqueous phase.
Figure 17B:
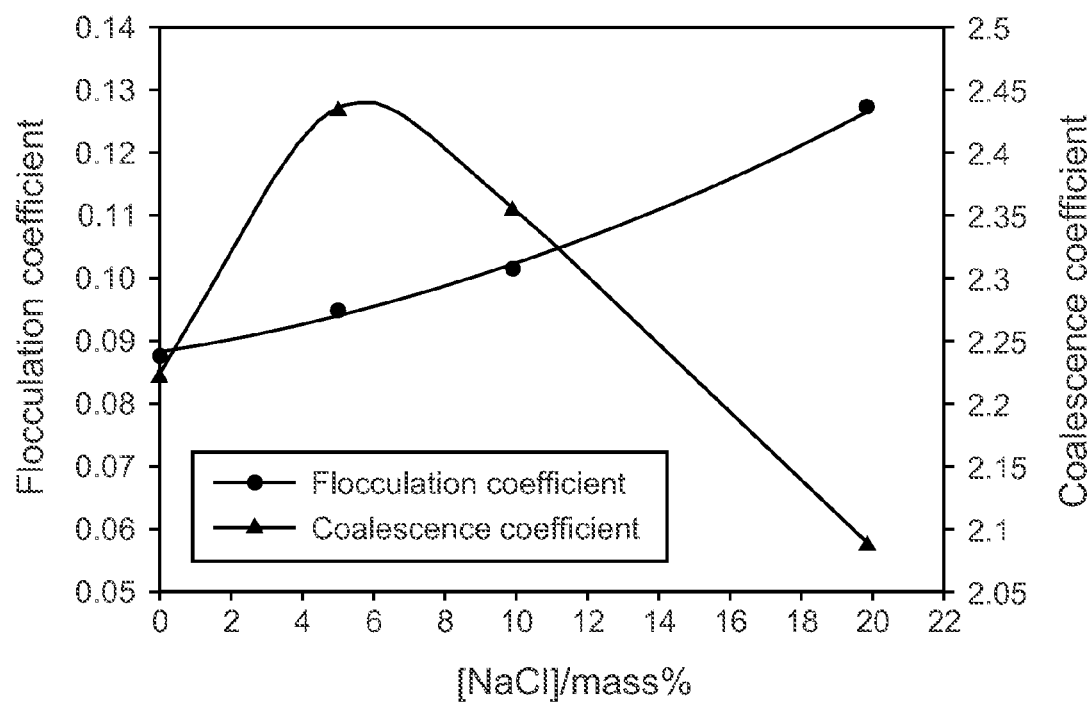
FIG. 17B is a graph of the values of $C_f$ and $C_c$ as a function of the concentration of a sodium chloride solution.

The proposed linear relationship between CEF and $\phi^{-1}$ was found to be valid for all brine composition and concentration variations studied. This includes experimental work done with distilled water, sodium chloride solutions and synthetic brine made up according to a chemical analysis of the corresponding produced water. The IPR-CEF technique was used in an explorative investigation of the effect of aqueous phase composition on the mechanism of emulsion stabilization. Emulsions were made up with various sodium chloride concentrations. FIG. 17A shows the IPR-CEF relationships observed at different NaCl-concentrations of the aqueous phase. The flocculation coefficient, $C_f$, and coalescence coefficient, $C_c$, were derived form the slope and intercept of each experimental data set, using equation (9) and (10) respectively. The values of $C_f$ and $C_c$, as well as the correlation coefficient, $r^2$, are given in Table 1 and presented in FIG. 17B as a function of sodium chloride solution. In this case, flocculation appears to be hindered at higher brine concentration. Coalescence appears to be limited at an optimum brine concentration, but high brine concentration seems to facilitate coalescence in the system studied. The IPR-CEF technique was found to be useful in research related to the understanding of the role of aqueous phase composition on crude oil emulsion stability.

Figure 18A:
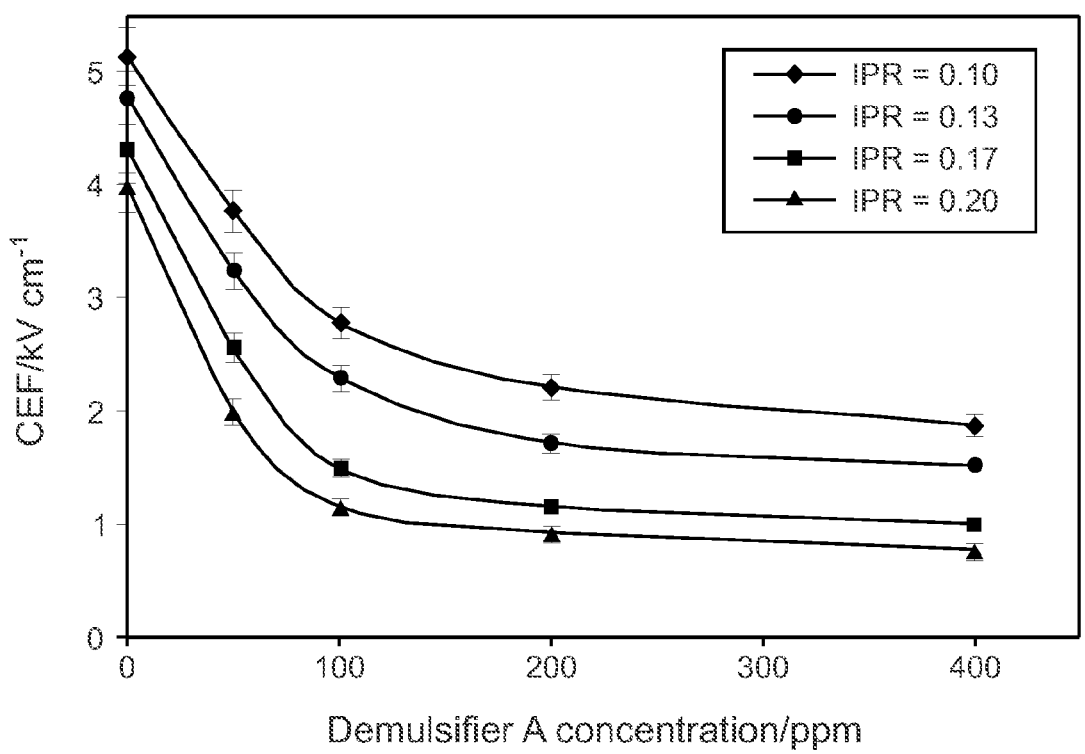
FIG. 18A shows CEF measurements as a function of chemical demulsifier concentration.
Figure 18B:
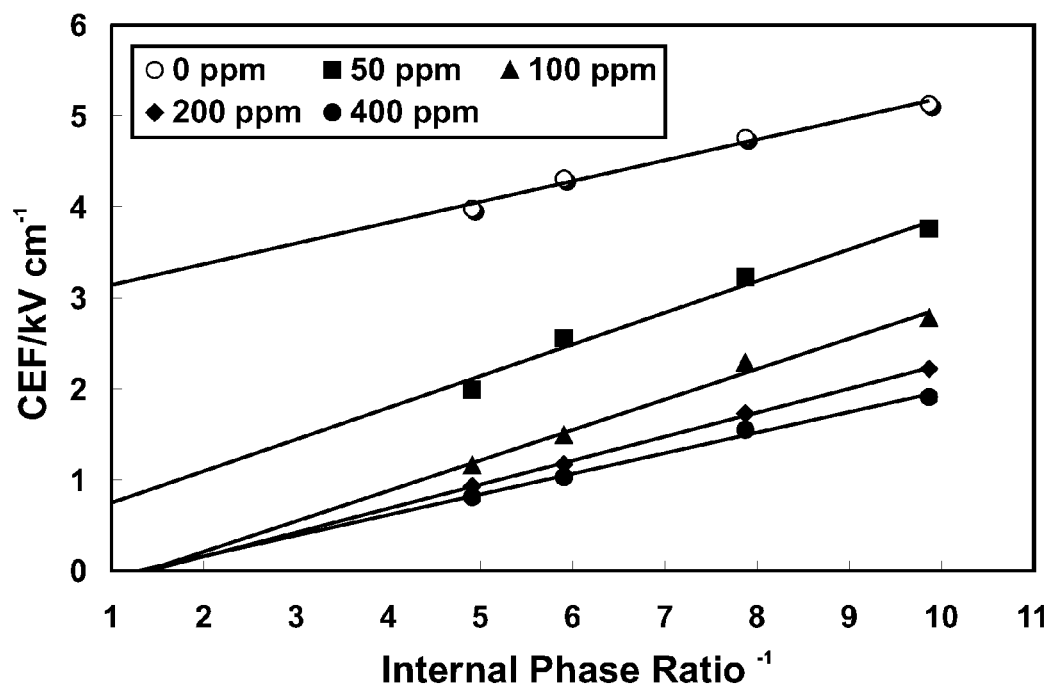
FIG. 18B is an IPR-CEF plot illustrating that the proposed linear relationship between CEF and $\phi^{-1}$ was found to be valid for all the experiments in the presence of chemical demulsifiers.
Figure 18C:
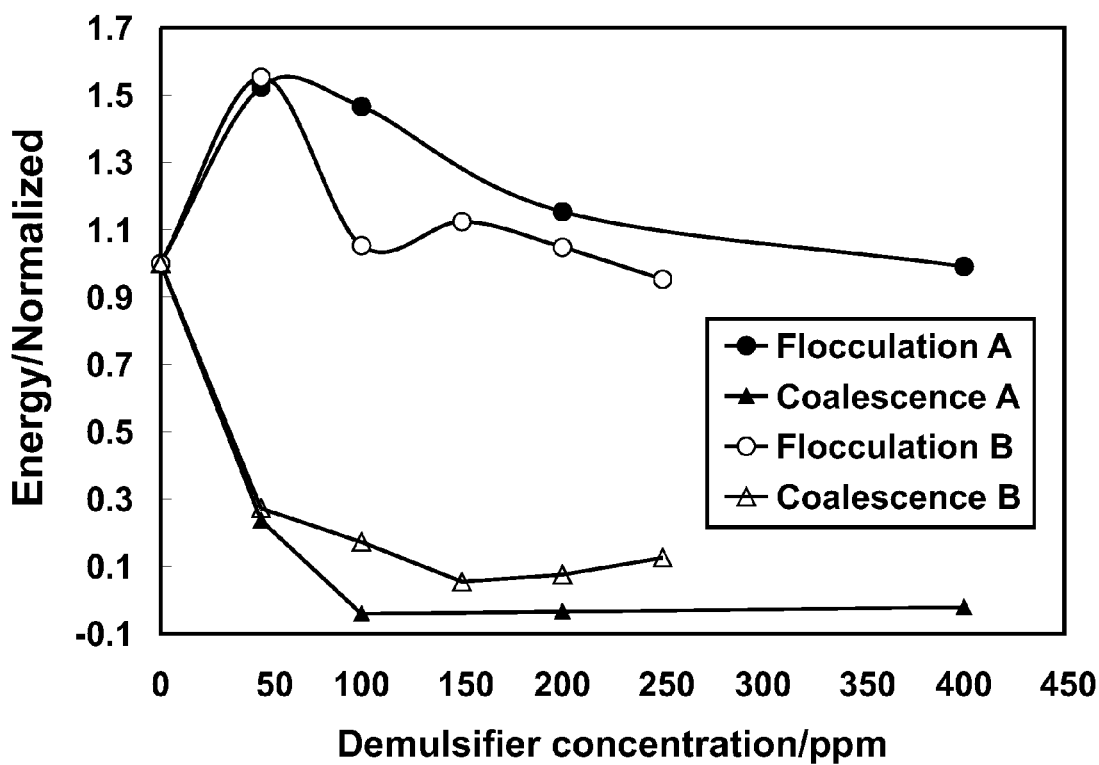
FIG. 18C is a graphical comparison of the relative energy involved in the flocculation as well as coalescence steps of demulsification with respect to both the two chemical demulsifiers.

The effect of chemical demulsifier on emulsion stability is clearly visible by CEF measurement as shown in FIG. 18A. The proposed linear relationship between CEF and $\phi^{-1}$ was found to be valid for all the experiments in the presence of chemical demulsifiers, as indicated in FIG. 18B. Flocculation and coalescence coefficients, $C_f$ and $C_c$, were calculated from experimental results in the absence, as well as at various concentrations of both chemical demulsifiers A and B. Some of the results are listed as Dem A and Dem B in Table 1, under the chemical additive column, Chem. The mechanism of demulsification by a chemical demulsifier can be evaluated in terms of the relative amount of energy required for both flocculation and coalescence, by calculating the ratio of both coefficients, $C_f$ and $C_c$, as determined for treated and untreated emulsions. Results from such calculations are shown in FIG. 18C, and offer insight into the mechanism of demulsification by the chemical demulsifiers. The primary effect of both chemical demulsifiers is a significant reduction in energy requirement for coalescence. Demulsifier A shows the highest reduction in the barrier to coalescence and maintain this effect over the concentration range studied. Demulsifier B has less effect and indicates a tendency to lose advantage at higher concentrations. This effect is well known and generally referred to as "over treat". With respect to flocculation behavior of the emulsion, both demulsifiers shows a secondary opposing effect to increase the energy requirement for flocculation in an optimum range. Demulsifier A is more prominent in this effect and appears to be reluctant to benefit flocculation even at relative high dosages. It is believed that the proposed IPR-CEF technique can be valuable in quantitative structure activity relationship (QSAR) studies to gain knowledge on the mechanism of chemical demulsifier function.

Experimental results from this study support the proposed linear relationship between CEF-data and the corresponding inverse internal phase ratio. This relationship was found to be valid for all emulsion systems, made up from the under identical conditions with a certain degree of variation in the volume fraction of the aqueous phase. It is suggested that the flocculation coefficient, $C_f$, calculated from the slope of this linear relationship is a relative indication of the flocculation behavior, while the coalescence coefficient, $C_c$, calculated as the extrapolated CEF at $\phi^{-1}$, is an indication of the coalescence behavior of the emulsion system. The numerical value of these coefficients offers insight into the mechanism of emulsion stabilization which can be related to various variables such as the composition of the crude oil and aqueous phase, as well as emulsification conditions such as temperature, type of agitation and intensity of agitation. It has been shown that the effect of chemical demulsifiers can be studied by the application of the proposed IPR-CEF technique to reveal the mechanism of demulsification. It is believed that this technique is useful for quantitative structure activity relationship (QSAR) studies, to further our understanding of the mechanism of demulsifier function.

EXAMPLE 7

A series of mixtures were prepared, each mixture including a diluent, a hydrocarbon phase, and an aqueous phase. The investigated diluents included toluene, 20% heptane-80% toluene (H20T80), and 40% heptane-60% toluene (H40T60). The hydrocarbon phase was investigated at 2, 10 and 20 mass percent. The aqueous phase was deionized water at a concentration of either 4 or 10 volume percent. Each of these parameter series was emulsified (alternatively a basic emulsion of these components can be emulsified, then adjusted to form aliquots forming the basis of a parameter series) at atmospheric conditions (21° C.) by agitation for one minute with a Chandler Model 30-60 constant speed blender at 12,000 rpm. When a demulsifier was added, the emulsion was agitated a second time for 1 minute at 4,000 rpm.

The CEF measurements were made with parallel electrodes in a cavity at an electrode spacing of 1.6 mm using an AC voltage ramp to 2 kV at 150 V/s, sinusoidal at 340 Hz, with a threshold value set to 61 µA. Each emulsion was measured six times at one minute intervals and the average of the six measurements was used in data analysis as if it were a single CEF measurement.

Figure 19A:
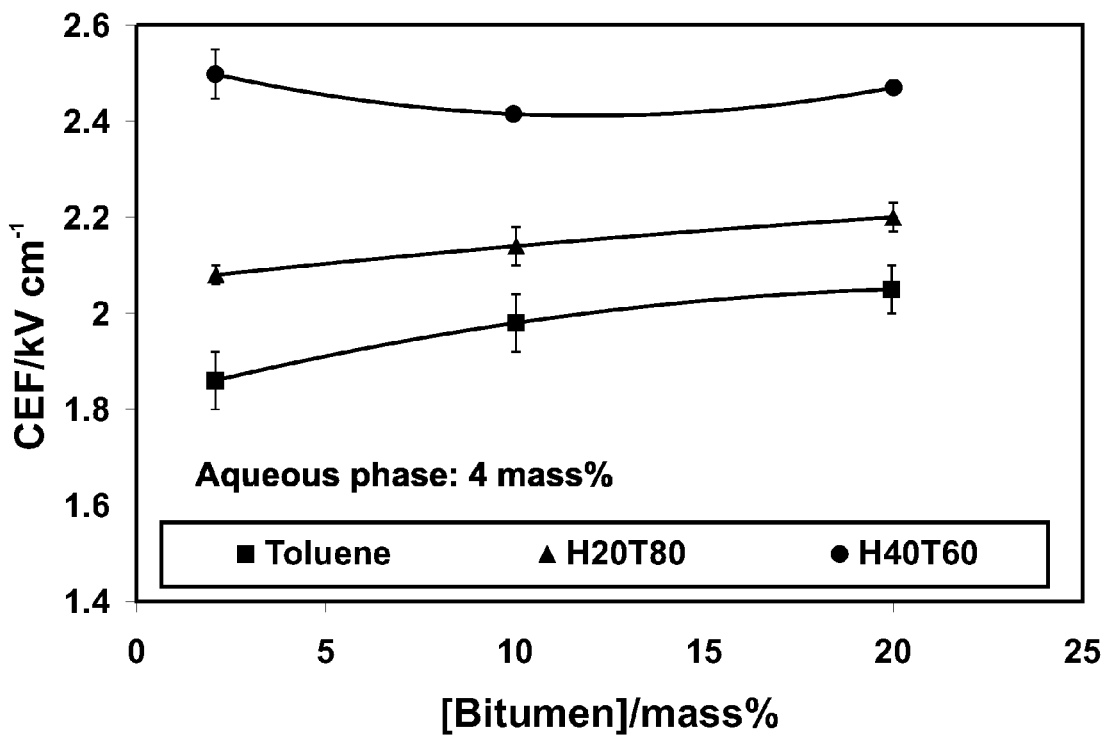
FIG. 19A-D are graphs that may be characterized as a CEF plot, an IPR-CEF plot, a $C_f$ plot, and a $C_c$ plot, respectively, that investigate the mechanism of emulsion stability of a bitumen emulsion as a function of the bitumen concentration.
Figure 19B:
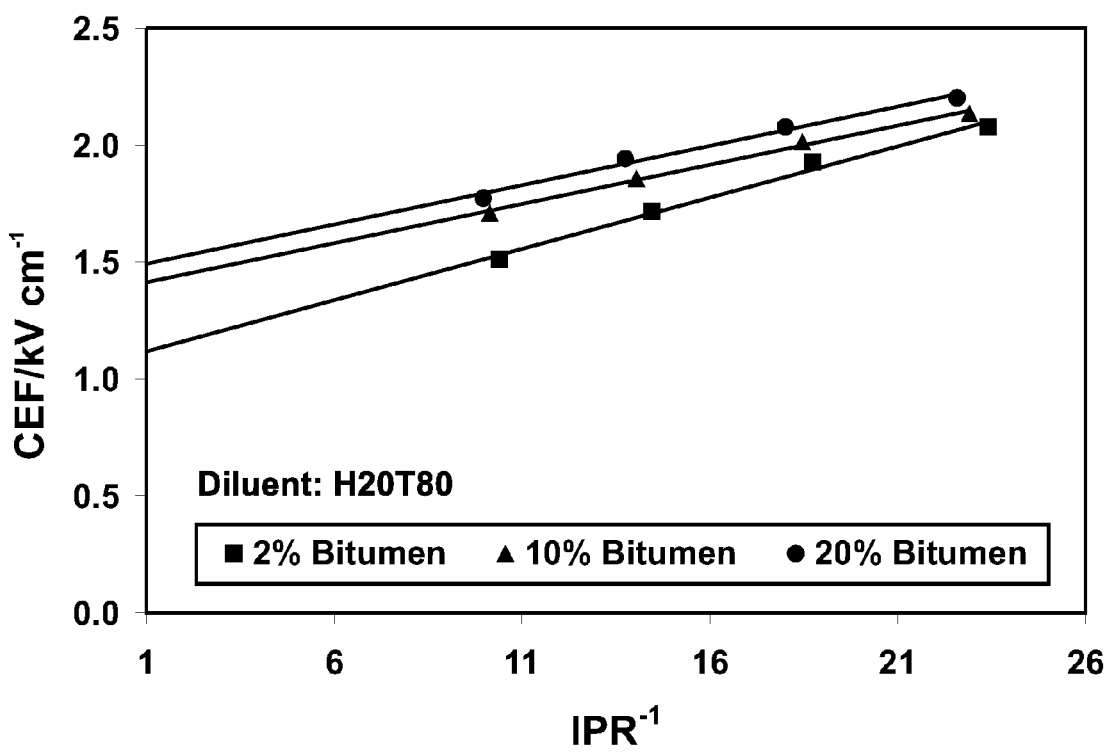
Figure 19C:
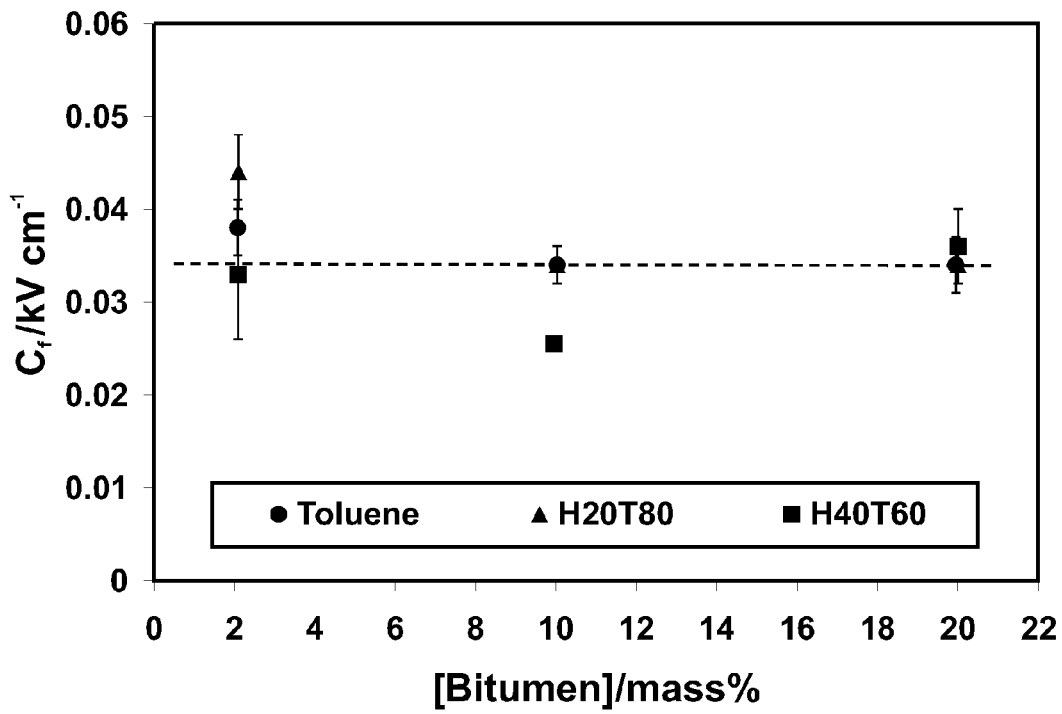
Figure 19D:
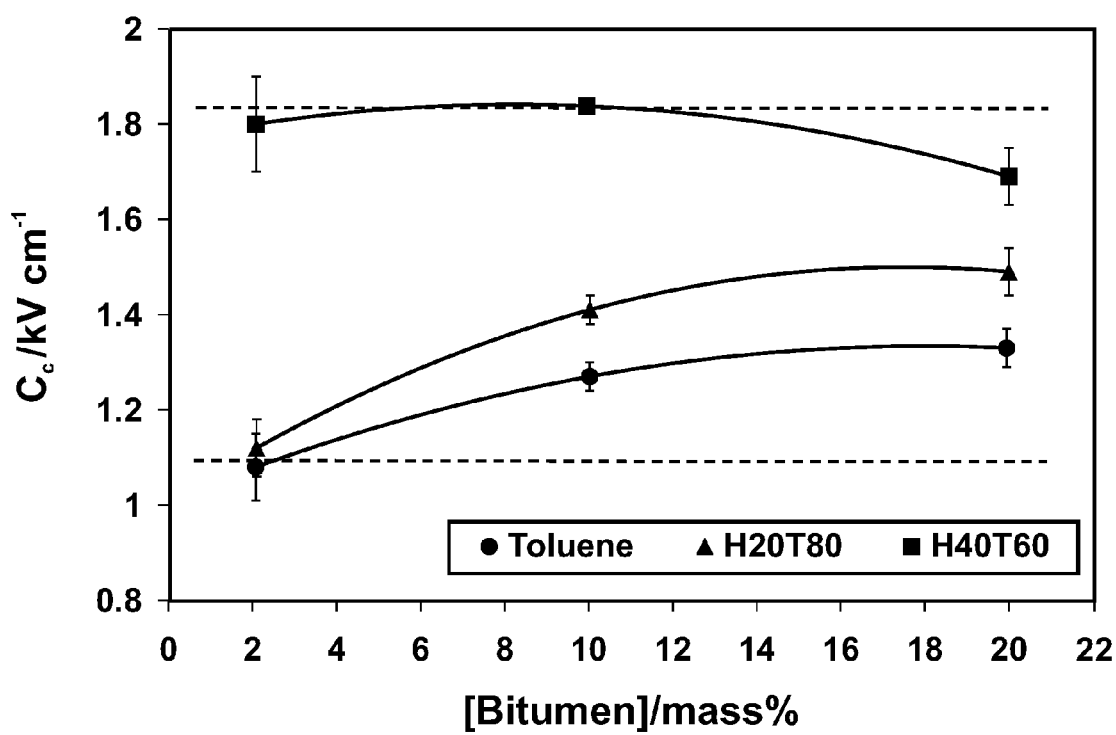

FIG. 19A-D are graphs that may be characterized as a CEF plot, an IPR-CEF plot, a $C_f$ plot, and a $C_c$ plot, respectively, that investigate the mechanism of emulsion stability of the bitumen emulsion as a function of the bitumen concentration. FIG. 19A shows a relatively small change in CEF over the bitumen concentration range of interest for all diluents, and that emulsion stability increased with aliphatic diluent character. FIG. 19B shows a prominent variation in coalescence behaviour. FIG. 19C shows little change in flocculation behaviour over the bitumen concentration range. FIG. 19D shows that the coalescence behaviour is influenced by bitument concentration, but the extent of the effect depends upon the diluent character. While many observations may result from the present IPR-CEF techniques and graphs, only select observations are mentioned below. Other observations will be apparent to those of ordinary skill in the art after gaining an understanding of the present invention.

Figure 20A:
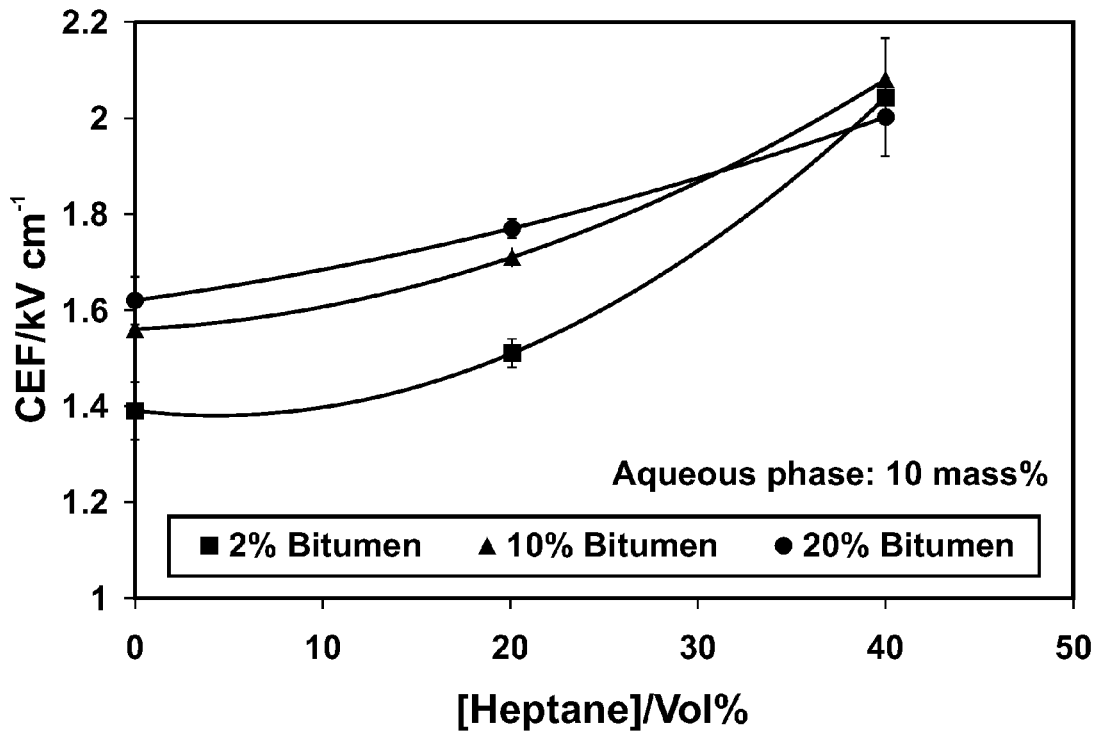
FIG. 20A-D are graphs that may be characterized as a CEF plot, an IPR-CEF plot, a $C_f$ plot, and a $C_c$ plot, respectively, that investigate the mechanism of emulsion stability of the same bitumen emulsion as a function of the diluent character.
Figure 20B:
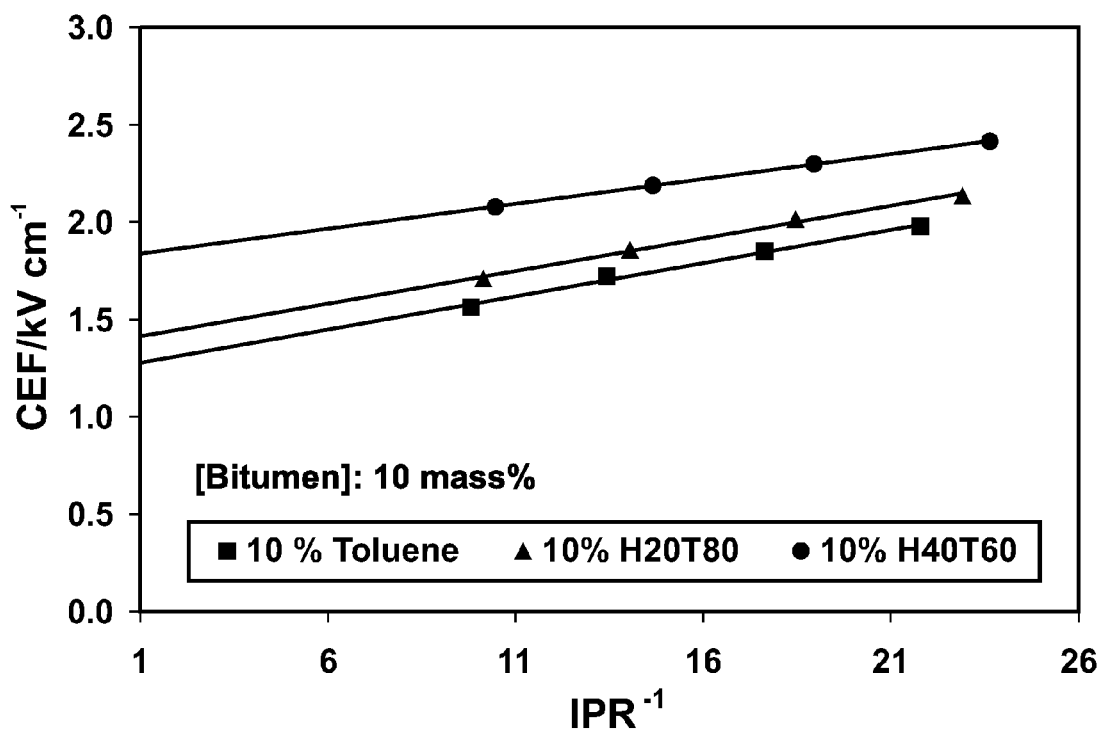
Figure 20C:
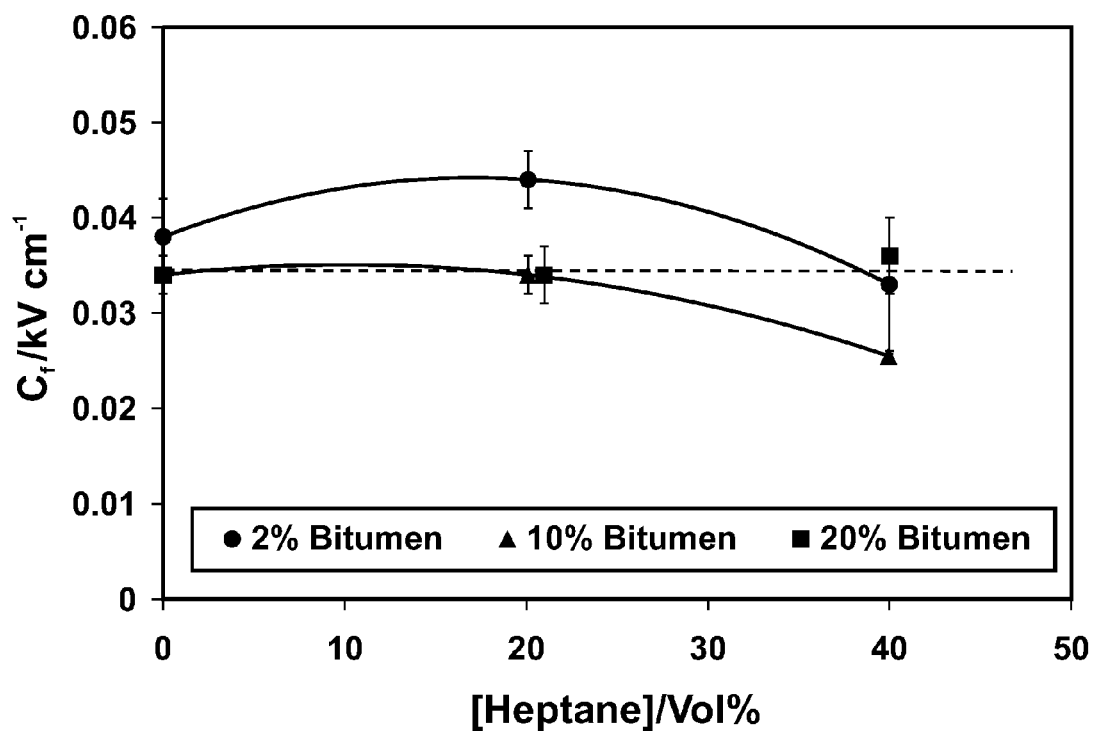
Figure 20D:
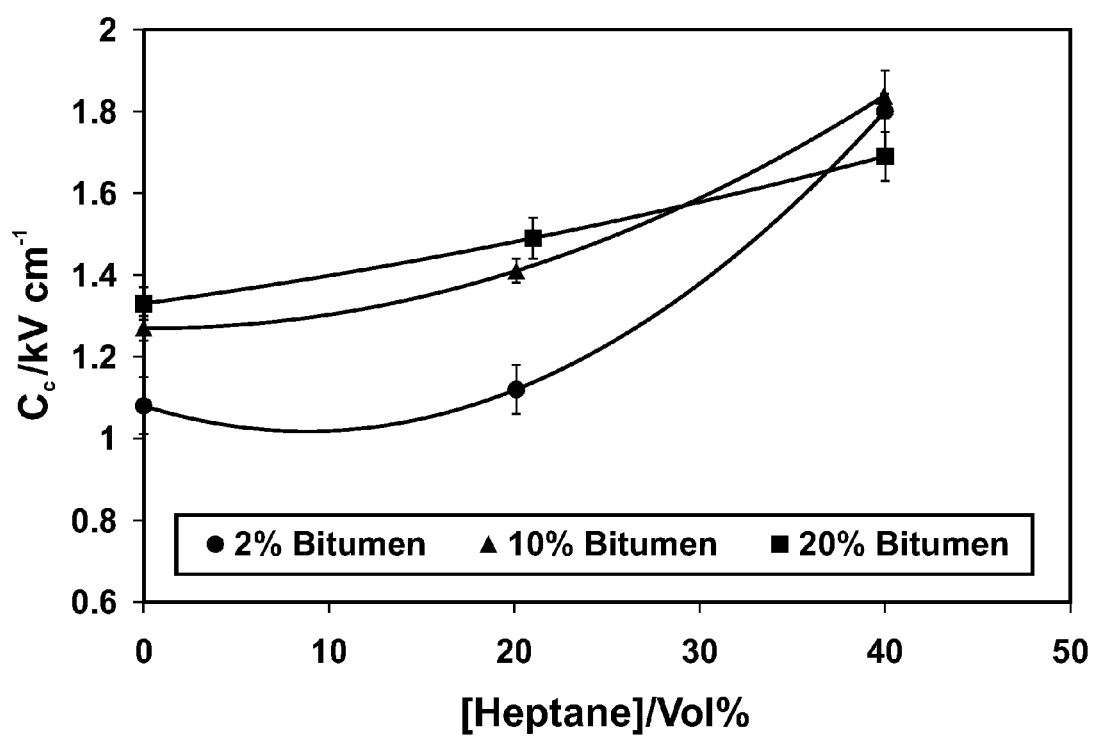

FIG. 20A-D are graphs that may be characterized as a CEF plot, an IPR-CEF plot, a $C_f$ plot, and a $C_c$ plot, respectively, that investigate the mechanism of emulsion stability of the same bitumen emulsion as a function of the diluent character. FIGS. 20C and 20D show that diluent character has little effect on flocculation behaviour, but a significant effect on coalescence behaviour.

Figure 21A:
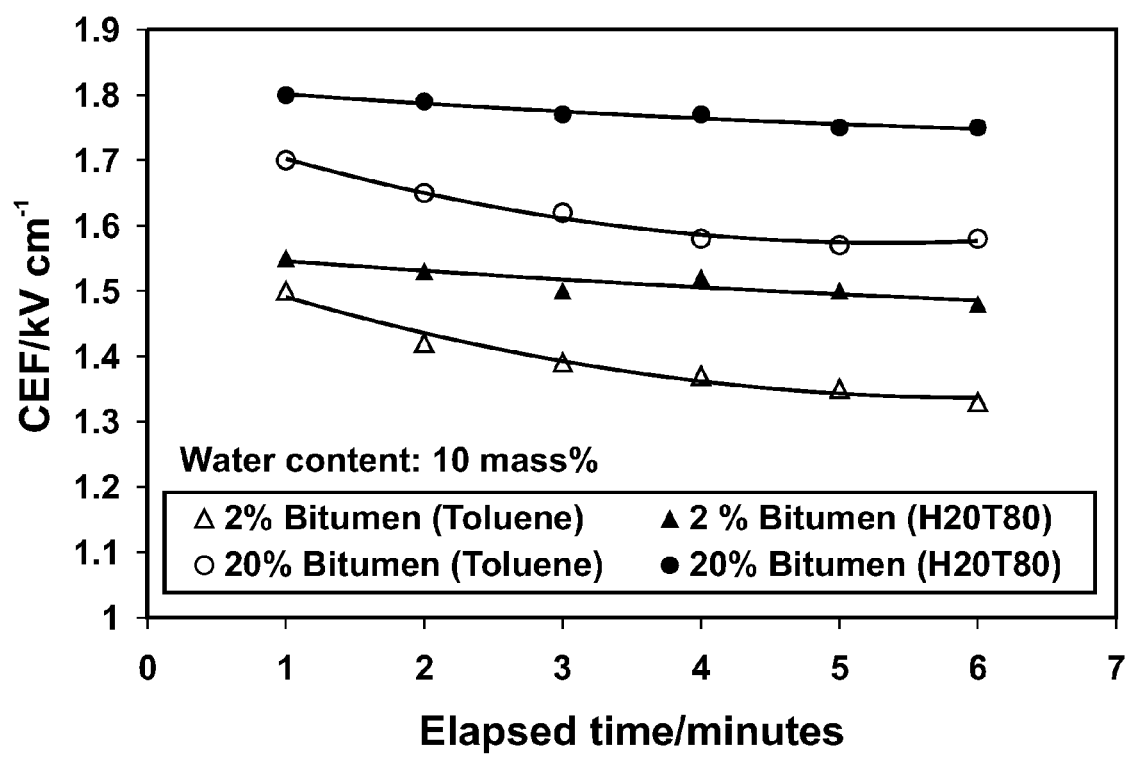
FIG. 21A-C are graphs that may be characterized as a CEF plot, a $C_f$ plot, and a $C_c$ plot, respectively, that investigate the mechanism of emulsion stability of the same bitumen emulsion as a function of time.
Figure 21B:
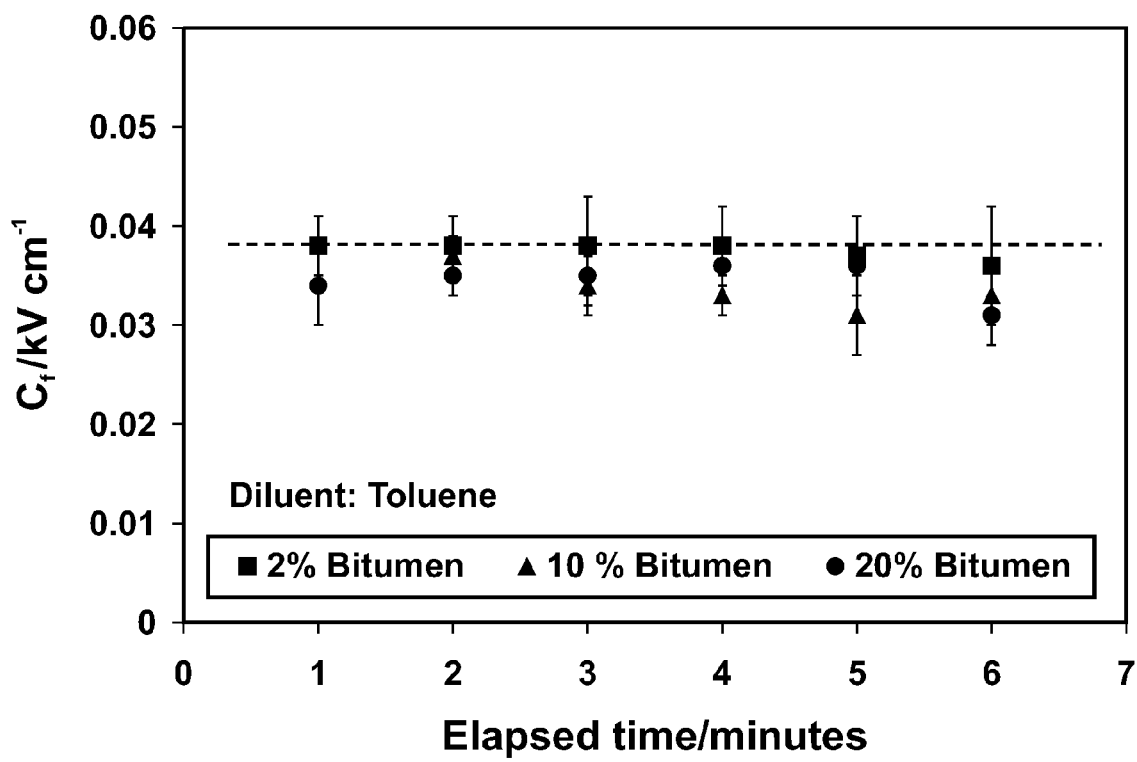
Figure 21C:
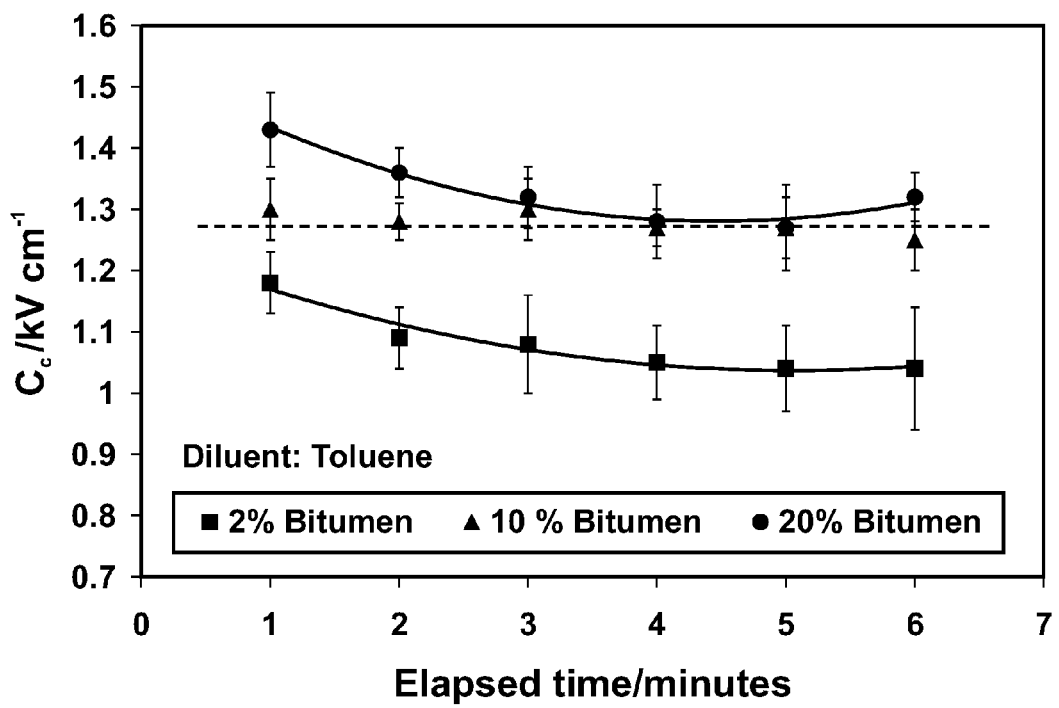

FIG. 21A-C are graphs that may be characterized as a CEF plot, a $C_f$ plot, and a $C_c$ plot, respectively, that investigate the mechanism of emulsion stability of the same bitumen emulsion as a function of time.

Figure 22A:
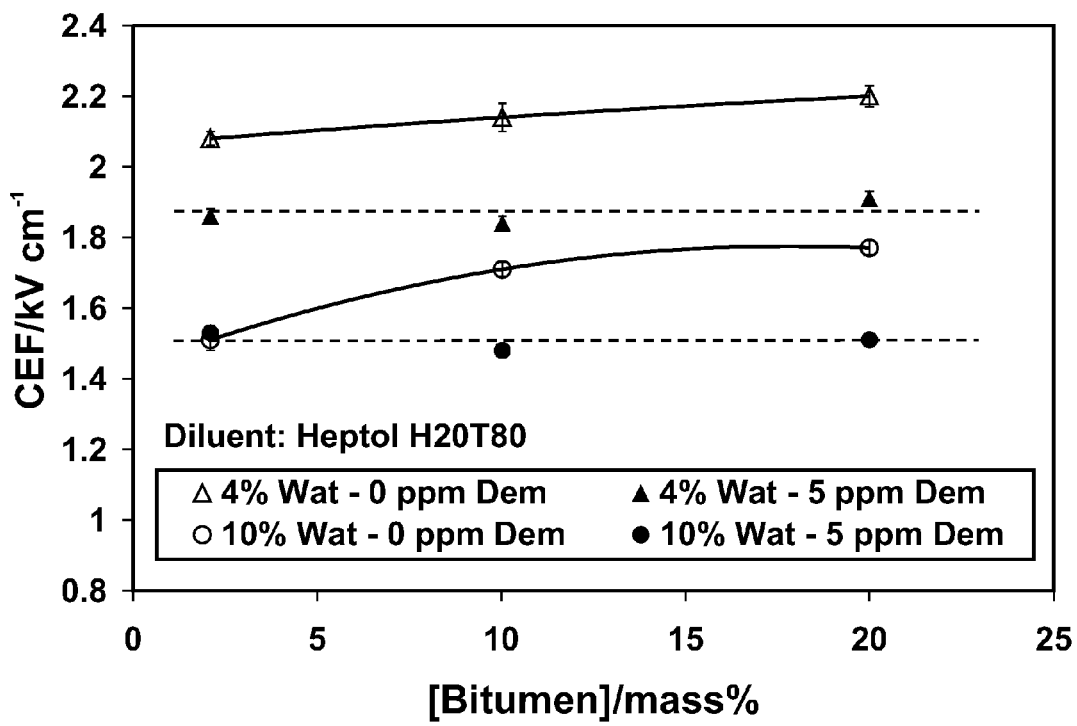
FIG. 22A-E are graphs that may be characterized as a CEF plot, an IPR-CEF plot, a $C_f$ plot, a $C_c$ plot, and a normalized energy plot, respectively, that investigate the mechanism of emulsion stability of the same bitumen emulsion as a function of bitumen concentration in the presence or absence of a chemical demulsifier additive.
Figure 22B:
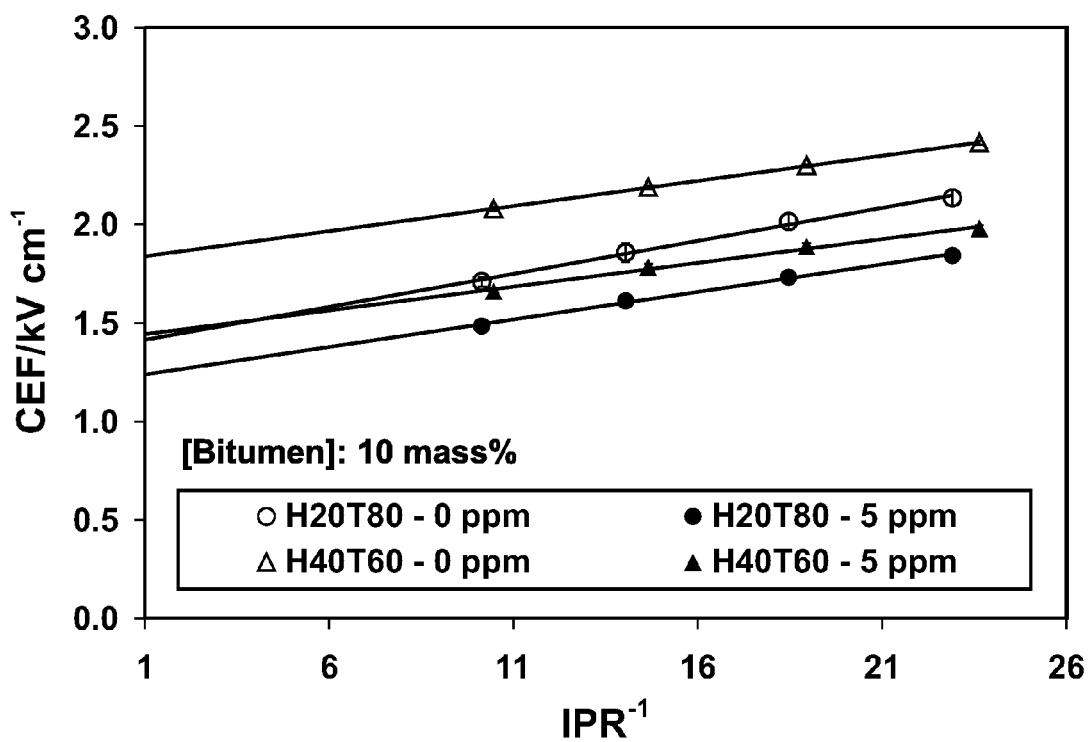
Figure 22C:
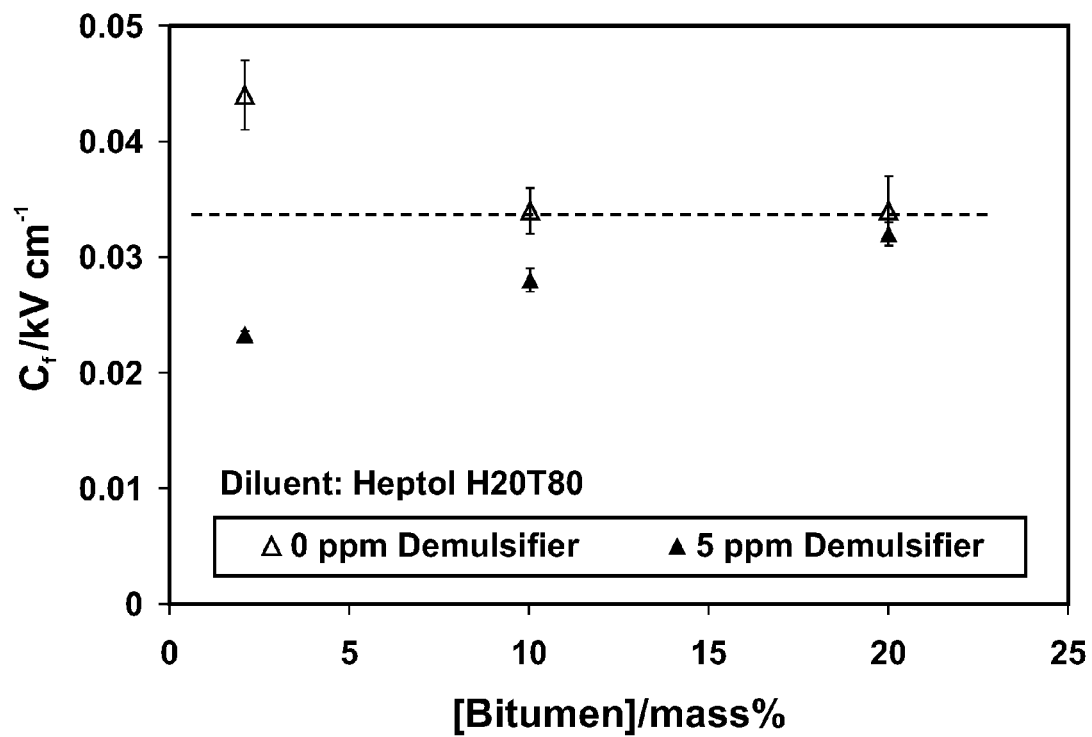
Figure 22D:
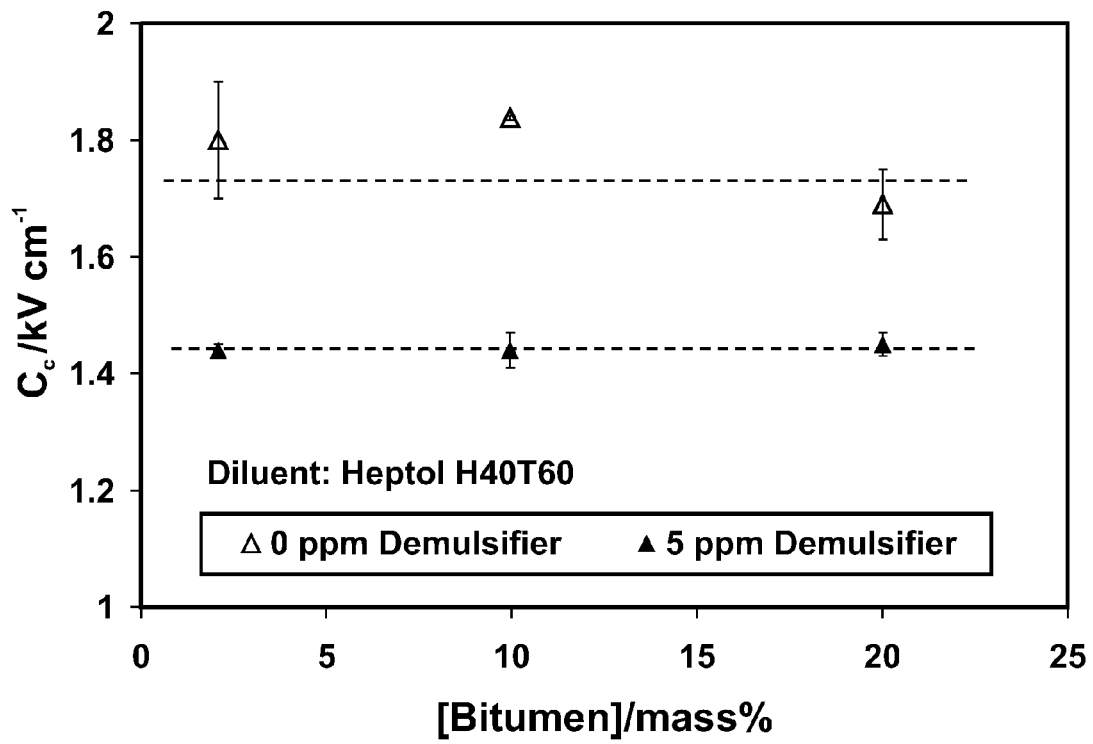
Figure 22E:
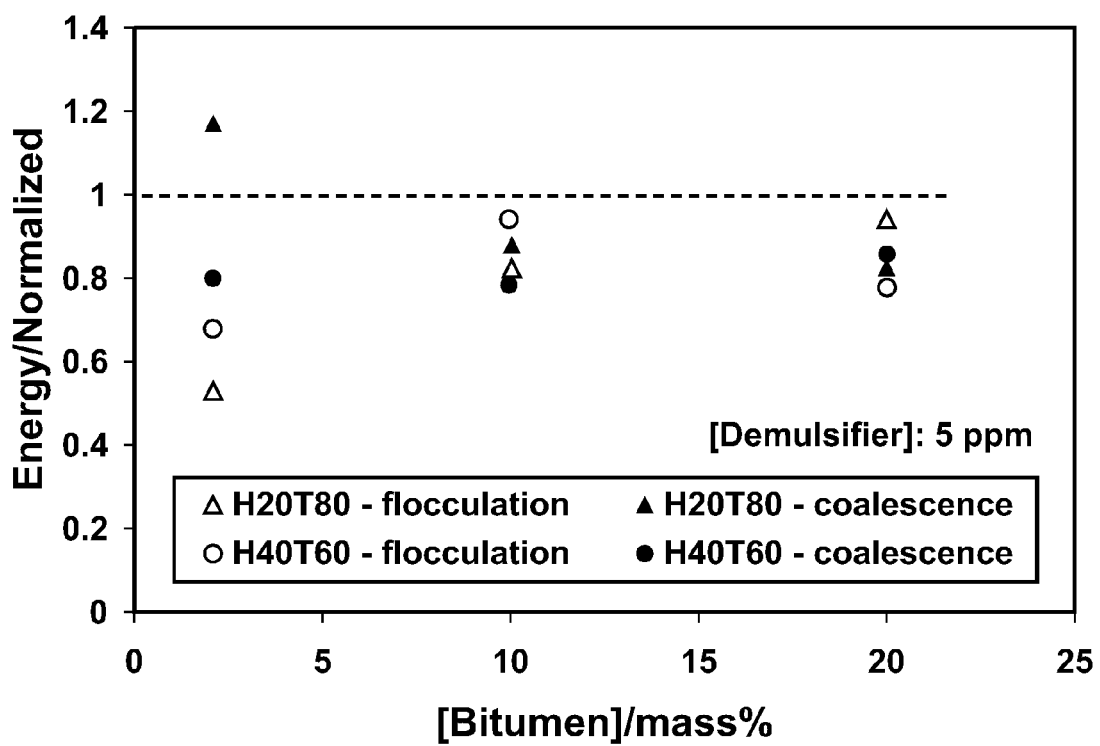
Figure 23:
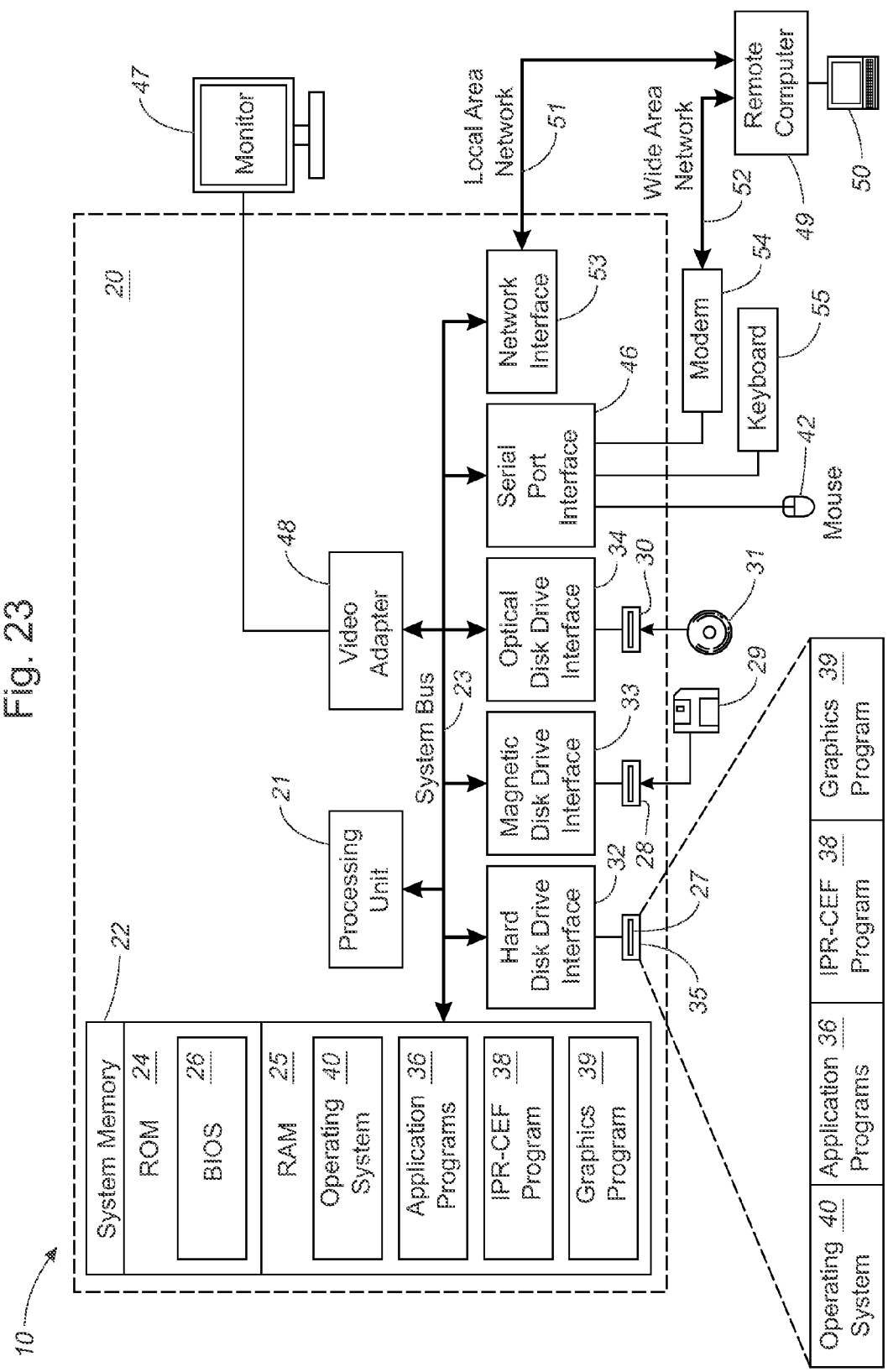
FIG. 23 is a schematic diagram of a system that is suitable for updating a dictionary on a computer system.

FIG. 22A-E are graphs that may be characterized as a CEF plot, an IPR-CEF plot, a $C_f$ plot, a $C_c$ plot, and a normalized energy plot, respectively, that investigate the mechanism of emulsion stability of the same bitumen emulsion as a function of bitumen concentration in the presence or absence of a chemical demulsifier additive. FIG. 22B shows a prominent change in coalescence behaviour in the presence of 5 ppm of a chemical demulsifier FIG. 23 is a schematic diagram of a system that is suitable for performing IPR-CEF calculations and/or graphs on a computer system or even controlling an automated IPR-CEF system. The system 10 includes a general-purpose computing device in the form of a conventional personal computer 20. Generally, a personal computer 20 includes a processing unit 21, a system memory 22, and a system bus 23 that couples various system components including the system memory 22 to processing unit 21. System bus 23 may be any of several types of bus structures including a memory bus or memory controller, a peripheral bus, and a local bus using any of a variety of bus architectures. The system memory includes a read only memory (ROM) 24 and random access memory (RAM) 25. A basic input/output system (BIOS) 26, containing the basic routines that help to transfer information between elements within personal computer 20, such as during start-up, is stored in ROM 24.

Personal computer 20 further includes a hard disk drive 35 for reading from and writing to a hard disk 27, a magnetic disk drive 28 for reading from or writing to a removable magnetic disk 29, and an optical disk drive 30 for reading from or writing to a removable optical disk 31 such as a CD-ROM or other optical media. Hard disk drive 35, magnetic disk drive 28, and optical disk drive 30 are connected to system bus 23 by a hard disk drive interface 32, a magnetic disk drive interface 33, and an optical disk drive interface 34, respectively. Although the exemplary environment described herein employs hard disk 27, removable magnetic disk 29, and removable optical disk 31, it should be appreciated by those skilled in the art that other types of computer readable media which can store data that is accessible by a computer, such as magnetic cassettes, flash memory cards, digital video disks, Bernoulli cartridges, RAMs, ROMs, and the like, may also be used in the exemplary operating environment. The drives and their associated computer readable media provide nonvolatile storage of computer-executable instructions, data structures, program modules, and other data for personal computer 20. For example, the operating system 40 and application programs 36 may be stored in the RAM 25 and/or hard disk 27 of the personal computer 20.

A user may enter commands and information into personal computer 20 through input devices, such as a keyboard 55 and a pointing device 42. Other input devices (not shown) may include a microphone, joystick, game pad, satellite dish, scanner, or the like. These and other input devices are often connected to processing unit 22 through a serial port interface 46 that is coupled to the system bus 23, but may be connected by other interfaces, such as a parallel port, game port, a universal serial bus (USB), or the like. A display device 47 may also be connected to system bus 23 via an interface, such as a video adapter 48. In addition to the monitor, personal computers typically include other peripheral output devices (not shown), such as speakers and printers.

The personal computer 20 may operate in a networked environment using logical connections to one or more remote computers 49. Remote computer 49 may be another personal computer, a server, a client, a router, a network PC, a peer device, a mainframe, a personal digital assistant, an Internet-connected mobile telephone or other common network node. While a remote computer 49 typically includes many or all of the elements described above relative to the personal computer 20, only a memory storage device 50 has been illustrated in the figure. The logical connections depicted in the figure include a local area network (LAN) 51 and a wide area network (WAN) 52. Such networking environments are commonplace in offices, enterprise-wide computer networks, intranets, and the Internet.

When used in a LAN networking environment, the personal computer 20 is often connected to the local area network 51 through a network interface or adapter 53. When used in a WAN networking environment, the personal computer 20 typically includes a modem 54 or other means for establishing high-speed communications over WAN 52, such as the Internet. Modem 54, which may be internal or external, is connected to system bus 23 via serial port interface 46. In a networked environment, program modules depicted relative to personal computer 20, or portions thereof, may be stored in the remote memory storage device 50. It will be appreciated that the network connections shown are exemplary and other means of establishing a communications link between the computers may be used.

A number of program modules may be stored on hard disk 27, magnetic disk 29, optical disk 31, ROM 24, or RAM 25, including an operating system 40, application programs 36, the IPR-CEF program 38 and an installed graphics program 39 into which the IPR-CEF data 38 will be shared. Program modules include routines, sub-routines, programs, objects, components, data structures, etc., which perform particular tasks or implement particular abstract data types. Aspects of the present invention may be implemented in the form of an application program 36 and/or a graphics program 39 associated with IPR-CEF program 38. The application program 36 generally comprises computer-executable instructions for, inter alia, identifying the installed graphics program 39 and updating the program 39 with data from the IPR-CEF program 38. The installed program 38 generally comprises computer-executable instructions for providing the IPR-CEF process (not shown).

The described example shown in FIG. 23 does not imply architectural limitations. For example, those skilled in the art will appreciate that the present invention may be implemented in other computer system configurations, including hand-held devices, multiprocessor systems, microprocessor based or programmable consumer electronics, network personal computers, minicomputers, mainframe computers, and the like. The invention may also be practiced in distributed computing environments, where tasks are performed by remote processing devices that are linked through a communications network. In a distributed computing environment, program modules may be located in both local and remote memory storage devices.

It should be recognized therefore, that embodiments of the present invention may take the form of an entirely hardware embodiment, an entirely software embodiment or an embodiment containing both hardware and software elements. In particular embodiments, including those embodiments of methods, the invention may be implemented in software, which includes but is not limited to firmware, resident software and microcode.

Furthermore, the invention can take the form of a computer program product accessible from a computer-readable medium providing program code for use by or in connection with a computer or any instruction execution system. For the purposes of this description, a computer-usable or computer readable medium can be any apparatus that can contain, store, communicate, propagate or transport the program for use by or in connection with the instruction execution system, apparatus or device.

While inventive embodiments of methods are demonstrated in the following flow charts of the figures that follow, it should be realized that the demonstrated methods are exemplary methods provided by the present invention and may be implemented using computer code and/or a suitable system.

Figure 24A:
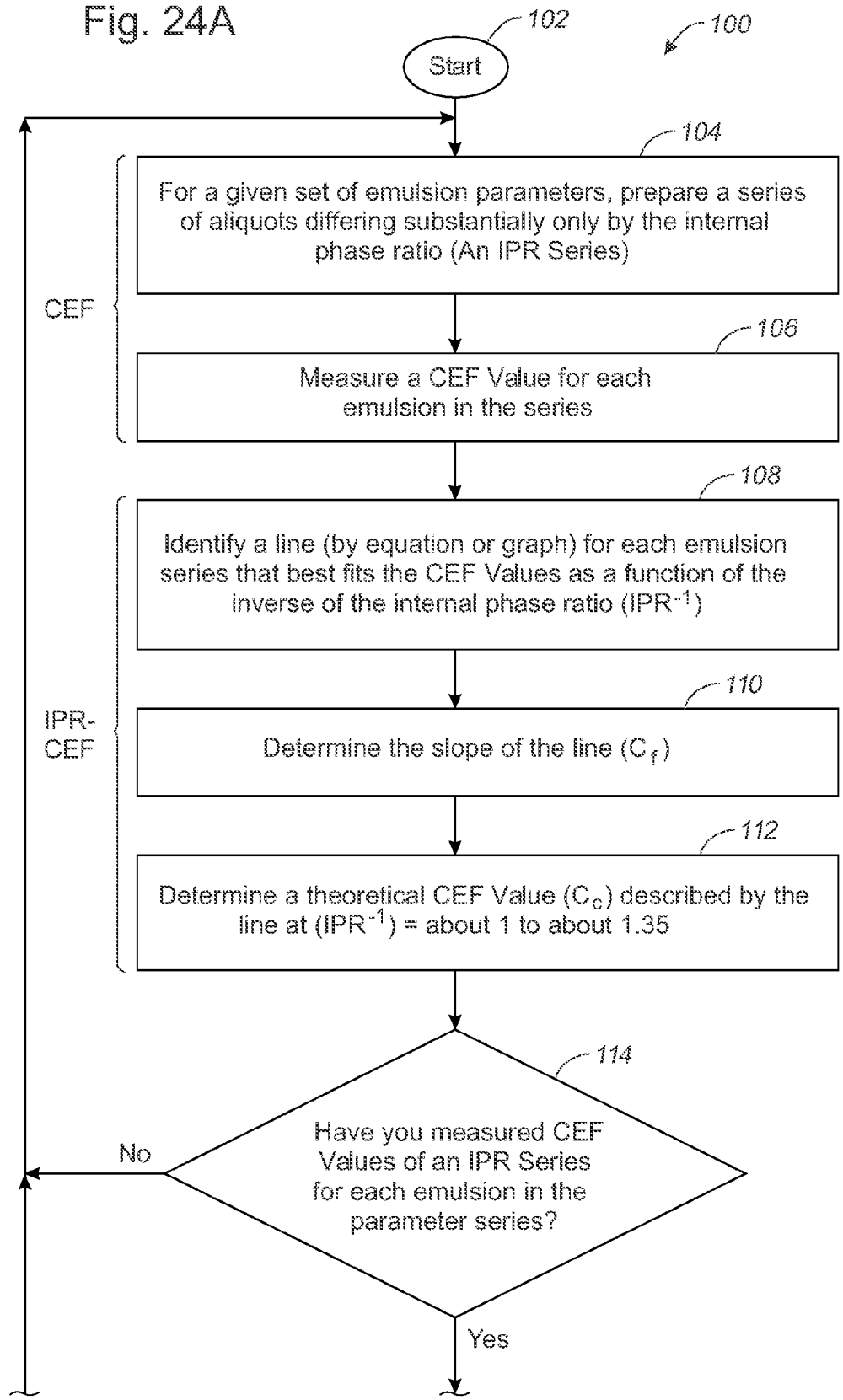
FIG. 24 is a flowchart of the IPR-CEF process including various optional steps.
Figure 24B:
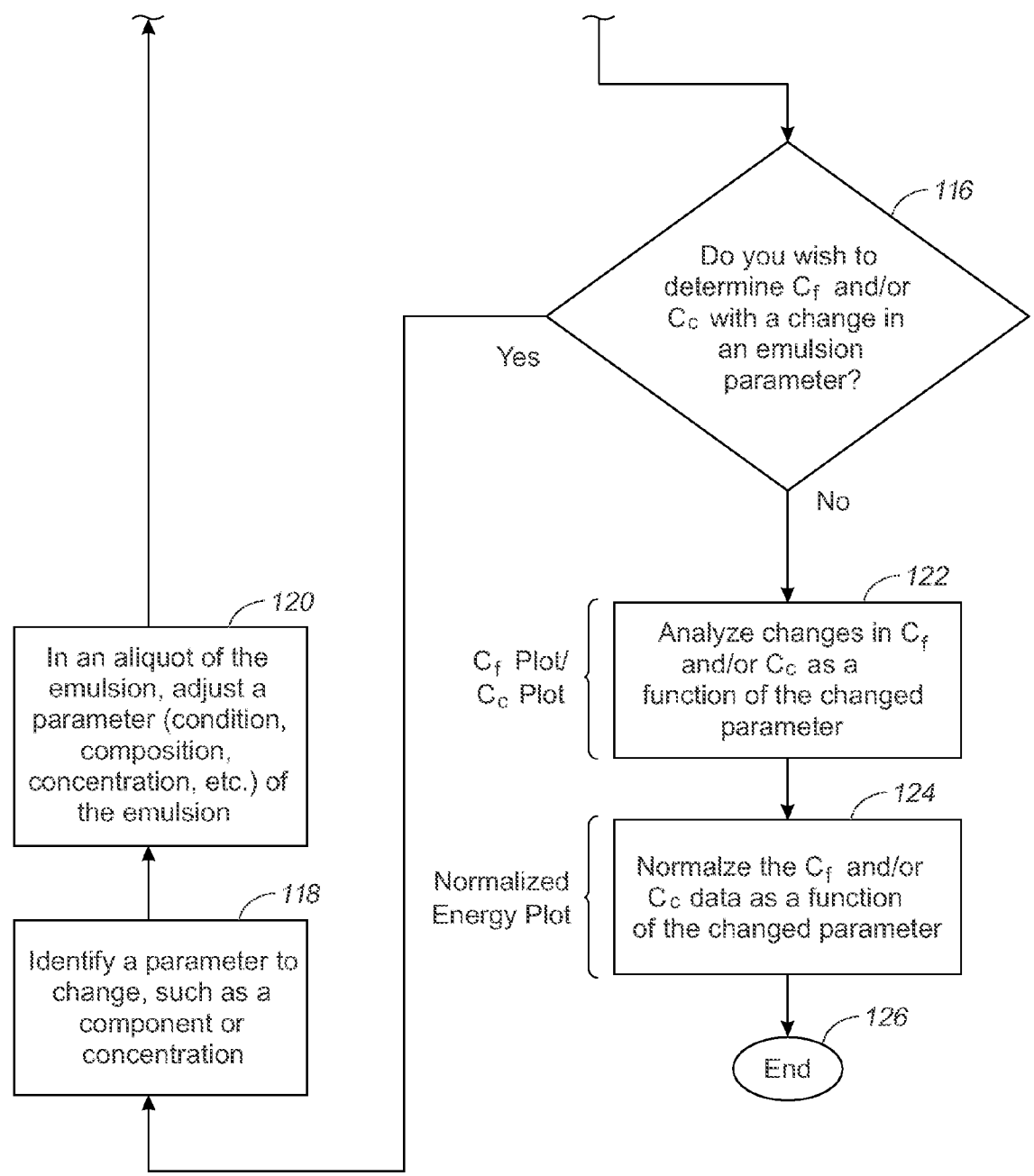

FIG. 24 is a flow chart of an exemplary method 100 for evaluating emulsion stability using critical electric field measurements. The method starts in state 102. In state 104, for a given set of emulsion parameters, a series of aliquots are prepared such that the aliquots differ substantially only by the internal phase ratio ("an IPR series"). State 106 includes measuring a CEF value for each emulsion in the IPR series. Most preferably, each emulsion is measured multiple times, such as six times, and the measurements are averaged, wherein the average CEF measurement is use in subsequent analysis. In state 108, a line is identified, such as with either by equation or graph, for each IPR emulsion series that best fits the CEF values as a function of the inverse of the internal phase ratio (IPR$^{-1}$). State 110 includes determining the slope of the line ($C_f$). In state 112, a theoretical CEF value ($C_c$) is determined, wherein the value is described by the line at an IPR$^{-1}$ of about 1 to about 1.35, preferably about 1.25 to about 1.45, and most preferably about 1.35. In state 114, if the CEF values of each emulsion aliquot in an IPR emulsion series have been measured for each emulsion aliquot in the parameter series, then the process continues to state 116. If these CEF values have not been measured for each aliquot in the parameter series, then the process returns back to state 104 to prepare another IPR emulsion series for another aliquot of the emulsion having the parameter adjusted to a different value.

In state 116, if a slope ($C_f$) and/or a theoretical CEF value ($C_c$) is to be determined with a change in an emulsion parameter, then the process continues to state 118. In state 118, an emulsion parameter to be changed is identified. Such a parameter could be any component, concentration, condition or other parameter of the emulsion. It should be recognized that the process is not limited to changing a single parameter at a time, but the process preferably changes only a single parameter in a parameter series so that the resulting change in the CEF can be directly attributed to the change. In state 120, a separate aliquot of the emulsion is obtained and the identified parameter is adjusted, before the procees continues to state 104. Typically, a parameter series will include two or more aliquots of the emulsion that are identical except that a common parameter, such as a demulsifier concentration, has been adjusted from one aliquot to the next aliquot in the parameter series. It should be recognized that the aliquots beneficially have the parameter adjusted across a range of values that are of interest.

In state 116, if a slope ($C_f$) and/or a theoretical CEF value ($C_c$) are not to be determined with a change in an emulsion parameter, or all of the parameters of interest have already been evaluated, then the process continues to state 122 where the changes in $C_f$ and/or $C_c$ as a function of the changed parameter(s) are analyzed. In state 124, the changes in $C_f$ and/or $C_c$ as a function of the changed parameter(s) may be normalized, such as in preparing a normalized energy plot. Finally, the process ends in state 126.

The process 100 is an exemplary process and includes many optional steps. States 104, 106 and 108 are deemed necessary steps to the IPR-CEF process of the invention. At a minimum, important qualitative information can be obtained from these steps. In particular, it is possible to observe the relative energy barriers to flocculation and coalescence. Still, it is generally preferred to continue the process to states 110 and 112, which facilitate a quantitative evaluation of the emulsion stability by determining $C_f$ and/or $C_c$. Furthermore, a powerful analysis of emulsion stability can be gained by changing the value of a parameter of the emulsion, in accordance with states 118 and 120, then analyzing changes in $C_f$ and/or $C_c$ as a function of the changed parameter. A normalized energy plot according to state 124 may also prove helpful in analyzing and understanding the emulsion over a range of parameter values.

The terms "comprising," "including," and "having," as used in the claims and specification herein, shall be considered as indicating an open group that may include other elements not specified. The term "consisting essentially of," as used in the claims and specification herein, shall be considered as indicating a partially open group that may include other elements not specified, so long as those other elements do not materially alter the basic and novel characteristics of the claimed invention. The terms "a," "an," and the singular forms of words shall be taken to include the plural form of the same words, such that the terms mean that one or more of something is provided. For example, the phrase "a solution comprising a hydrocarbon-containing compound" should be read to describe a solution having one or more hydrocarbon-containing compound. The term "one" or "single" shall be used to indicate that one and only one of something is intended. Similarly, other specific integer values, such as "two," are used when a specific number of things is intended. The terms "preferably," "preferred," "prefer," "optionally," "may," and similar terms are used to indicate that an item, condition or step being referred to is an optional (not required) feature of the invention.

It should be understood from the foregoing description that various modifications and changes may be made in the preferred embodiments of the present invention without departing from its true spirit. It is intended that this foregoing description is for purposes of illustration only and should not be construed in a limiting sense. Only the language of the following claims should limit the scope of this invention.

What is claimed is:

1. A method comprising:
    determining a critical electric field value for each emulsion in a plurality of emulsion series, each emulsion series including emulsions that differ substantially only by internal phase volume ratios, and each emulsion series differing from each other emulsion series by a parameter of the emulsion other than internal phase volume ratio;
    evaluating, for each emulsion series, a line fit to the critical electric field values as a function of the inverse of the internal phase volume ratio for each emulsion in the emulsion series, wherein the step of evaluating further comprises determining the slope of the line, extrapolating the line to determine a theoretical critical electric field value at an internal phase volume ratio of about one, or combinations thereof; and
    communicating the theoretical critical electric field value, the slope of the line, or both to a user.

2. The method of claim 1, wherein the step of evaluating comprises determining the slope of the line, the method farther comprising:
    comparing the slope determined for each emulsion series.

3. The method of claim 2, wherein the plurality of emulsion series comprise a control and at least one emulsion series differing from the control by inclusion of a demulsifier composition.

4. The method of claim 3, wherein the plurality of emulsion series comprise a control, at least one emulsion series differing from the control by inclusion of a first demulsifier composition, and at least one emulsion series differing from the control by inclusion of a second demulsifier composition.

5. The method of claim 4, further comprising:
    comparing the slope determined for the at least one emulsion series including the first demulsifier with the slope determined for the at least one emulsion series including the second demulsifier.

6. The method of claim 5, further comprising:
    calculating a relative energy value for each emulsion series by dividing the slope determined for that emulsion series by the slope determined for the control.

7. The method of claim 6, wherein the plurality of emulsion series includes emulsion series that differ by a secondary parameter, the method further comprising:
    plotting the relative energy value for each emulsion series as a function of the secondary parameter.

8. The method of claim 6, further comprising:
    identifying the relative energy value is a relative indicator of the flocculation energy barrier.

9. The method of claim 5, further comprising:
    calculating a relative energy value for each emulsion series by dividing the theoretical CEF determined for that emulsion series by the theoretical CEF determined for the control.

10. The method of claim 9, further comprising:
    identifying the theoretical CEF value as a relative indicator of the coalescence energy barrier.

11. The method of claim 10, further comprising:
    evaluating the first and second demulsifier by their relative ability to effect the flocculation energy barrier, the coalescence energy baffler, or a combination thereof.

12. The method of claim 9, wherein the plurality of emulsion series includes emulsion series that differ by a secondary parameter, the method further comprising:
    plotting the relative energy value for each emulsion series as a function of the secondary parameter.

13. The method of claim 5, further comprising:
    selecting the demulsifier associated with the emulsion series having the lesser slope.

14. The method of claim 2, further comprising:
    identifying the slope as a relative indicator of the flocculation energy barrier.

15. The method of claim 4, further comprising:
    comparing the theoretical critical electric field value for the at least one emulsion series including the first demulsifier with the theoretical critical electric field value for the at least one emulsion series including the second demulsifier.

16. The method of claim 15, further comprising:
    selecting the demulsifier associated with the emulsion series having the lesser critical electric field value.

17. The method of claim 4, further comprising:
    comparing the theoretical critical electric field value for the emulsion series including the first demulsifier with the theoretical critical electric field value for the control.

18. The method of claim 4, further comprising:
    comparing the slope determined for the emulsion series including the first demulsifier with the slope determined for the control.

19. The method of claim 1, wherein the step of evaluating comprises extrapolating the line to determine a theoretical critical electric field value at an internal phase volume ratio of about one, the method farther comprising:
    comparing the theoretical critical field value determined for each emulsion series.

20. The method of claim 19, further comprising:
    evaluating the first and second demulsifier by their relative ability to effect the flocculation energy barrier, the coalescence energy baffler, or a combination thereof.

21. The method of claim 20, further comprising:
    selecting the demulsifier having the greater ability to effect the flocculation energy barrier, the coalescence energy barrier, or a combination thereof.

22. The method of claim 1, wherein the parameter is selected from temperature, pressure, demulsifier concentration, demulsifier species, external phase composition, internal phase concentrations, chemical structure, formulation of multiple component chemical compositions, and combinations thereof.

23. The method of claim 22, wherein the parameter is demulsifier concentration, the method flirt her comprising the step of:
    controlling the addition of demulsifier to a process according to the demulsifier concentration associated with an emulsion series having the lesser critical electric field value, the lesser slope, or both.

24. The method of claim 1, wherein the step of evaluating comprises determining the slope of the line, the method further comprising:
    comparing the slope determined for each emulsion series as a function of the parameter other than internal phase volume ratio.

25. The method of claim 24, further comprising:
repeating the steps of determining, evaluating and comparing for another emulsion series differing from the other emulsion series by the value, composition or quantity of the emulsion parameter.

26. The method of claim 1, wherein the step of evaluating comprises extrapolating the line to determine a theoretical critical electric field value at an internal phase volume ratio of about one, the method farther comprising:
comparing the theoretical critical field value determined for each emulsion series as a function of the parameter other than internal phase volume ratio.

27. The method of claim 26, further comprising:
repeating the steps of determining, evaluating and comparing for another emulsion series differing from the other emulsion series by the value, composition or quantity of the emulsion parameter.

28. The method of claim 1, wherein the step of determining a critical electric field value further comprises diluting and emulsifying an oil-containing sample with water at various internal phase volume ratios.

29. The method of claim 1, further comprising:
storing the theoretical critical electric field value, the slope of the line, or both in computer readable storage media.

30. The method of claim 1, further comprising:
forming the plurality of emulsion series.

31. A method comprising:
determining a critical electric field value for each emulsion in an emulsion series including emulsions that differ substantially only by internal phase volume ratios;
evaluating a line fit to the critical electric field values as a function of the inverse of the internal phase volume ratio for each emulsion in the emulsion series, wherein the step of evaluating further comprises determining the slope of the line, extrapolating the line to determine a theoretical critical electric field value at an internal phase volume ratio of about one, or combinations thereof; and
communicating the theoretical critical electric field value, the slope of the line, or both to a user.

32. The method of claim 31, further comprising:
identifying the slope of the line as a relative indicator of the flocculation energy barrier for the emulsion series.

33. The method of claim 31, further comprising:
identifying the theoretical critical electric field value as a relative indicator of the coalescence energy baffler for the emulsion series.

34. The method of claim 1, farther comprising:
forming the emulsion series.

35. The method of claim 1, further comprising:
storing the theoretical critical electric field value, the slope of the line, or both in computer readable storage media.

* * * * *